United States Patent
Sayler et al.

(10) Patent No.: US 6,544,729 B2
(45) Date of Patent: Apr. 8, 2003

(54) BIOLUMINESCENT BIOSENSOR DEVICE

(75) Inventors: Gary S. Sayler, Blaine, TN (US); Steven A. Ripp, Knoxville, TN (US); Bruce Applegate, West Lafayette, IN (US)

(73) Assignees: University of Tennessee, Knoxville, TN (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/910,360

(22) Filed: Jul. 20, 2001

(65) Prior Publication Data

US 2003/0027241 A1 Feb. 6, 2003

(51) Int. Cl.[7] .............................. C12O 1/00; C12O 1/66; C12O 1/68; C12O 1/70; G01N 33/53; G01N 33/567; G01N 33/554; G01N 33/569; G01N 21/64; G01N 21/66

(52) U.S. Cl. .................... 435/5; 435/4; 435/6; 435/7.2; 435/7.32; 435/8; 422/82.08

(58) Field of Search ...................... 210/603; 73/864.31; 530/402; 435/8, 4, 5, 6, 7.2, 7.31–7.35, 7.72, 7.9, 7.91, 29, 30–35, 69.1, 91.1, 91.2, 170, 172.3, 183, 189, 235.1, 239, 252.2, 252.33, 287, 287.1, 288, 289, 291, 292, 316, 320.1; 424/9.1, 9.61, 193.1, 93.2; 426/2, 302, 335; 422/55, 57, 58, 82.01, 82.05, 82.06–82.08; 436/518, 524, 525, 531

(56) References Cited

U.S. PATENT DOCUMENTS

| | | | | |
|---|---|---|---|---|
| 4,209,585 A | * | 6/1980 | Lloyd et al. ............... 426/2 |
| 5,180,494 A | * | 1/1993 | Yamaguchi et al. ......... 210/603 |
| 5,447,836 A | * | 9/1995 | Wolber et al. .............. 435/170 |
| 5,663,069 A | * | 9/1997 | Ray et al. ................. 435/235.1 |
| 6,117,643 A | * | 9/2000 | Simpson et al. .............. 422/55 |
| 6,232,107 B1 | * | 5/2001 | Bryan et al. ................ 435/183 |

OTHER PUBLICATIONS

Dr. Graham Dark, On–Line Medical Dictionary, bacteriophage, Academic Medical Publishing & CancerWEB (1997).*
Merriam–Webster's Collegiate Dictionary, Tenth Edition, p. 85 (1998).0.*
Billard and DuBow, "Bioluminescence–Based Assays for Detection and Characterization of Bacteria and Chemicals in Clinicl Laboratories," Clinical Biochemistry, vol. 31, pp. 1–14.*
Applegate, B., C. Kelley, L. Lackey, J. McPherson, S. Kehrmeyer, F.–M. Menn, P. Bienkowski, and G. Sayler. 1997. "Pseudomonas Putida B2: A Tod–Lux Bioluminescent Reporter For Toluene and Trichloroethylene Co–Metabolism." *J. Ind. Microbiol. Biotech.* 18:4–9.
Applegate, B. M., S. R. Kehrmeyer, and G. S. Sayler. (Jul. 1998.) "A Chromosomally Based Tod–Luxcdabe WholeCell Reporter For Benzene, Toluene, Ethylbenzene, and Xylene (BTEX) Sensing." *Appl. Environ. Microbiol.* 64:2730–2735.
Bean, N. H., and P. M. Griffin. (Sep. 1990.) "Foodborne Outbreaks In The United States, 1973–1987: Pathogens, Vehicles, and Trends." *J. Food Protect.* 53:804–817.

(List continued on next page.)

*Primary Examiner*—James Housel
*Assistant Examiner*—Zachariah Lucas
(74) *Attorney, Agent, or Firm*—Akerman Senterfitt

(57) ABSTRACT

Disclosed are methods and devices for detection of bacteria based on recognition and infection of one or more selected strains of bacteria with bacteriophage genetically modified to cause production of an inducer molecule in the bacterium following phage infection. The inducer molecule is released from the infected bacterium and is detected by genetically modified bacterial bioreporter cells designed to emit bioluminescence upon stimulation by the inducer. Autoamplification of the bioluminescent signal permits detection of low levels of bacteria without sample enrichment. Also disclosed are methods of detection for select bacteria, and kits for detection of select bacteria based on the described technology.

27 Claims, 3 Drawing Sheets

OTHER PUBLICATIONS

Figure 1:
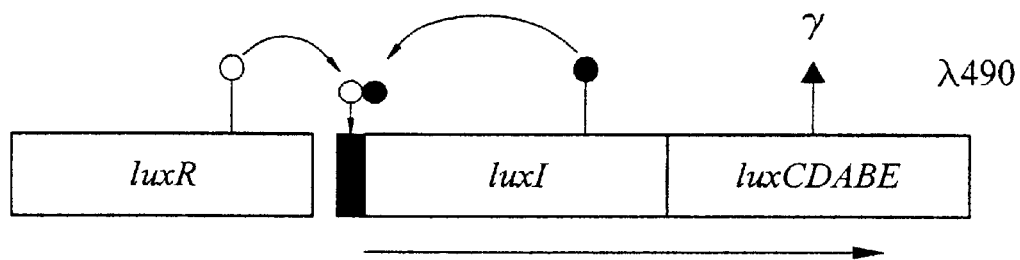

Berrang, M. E., R. E. Brackett, and L. R. Beuchat. (Oct. 1989.) "Growth Of Listeria monocytogenes On Fresh Vegetables Stored Under Controlled Atmosphere." *J. Food Protect.* 52:702–705.

Beuchat, L. R. 1996. "Listeria monocytogenes: Incidence On Vegetables." *Food Control* 7:223–228.

Beuchat, L. R., and R. E. Brackett. 1990. "Survival and Growth Of Listeria monocytogenes On Lettuce As Influenced by Shredding, Chlorine Treatment, Modified—Atmosphere Packaging and Temperature." *J. Food Sci.* 55:755–578.

Beuchat, L. R., and R. E. Brackett. (May 1991.) "Behavior Of Listeria monocytogenes Inoculated Into Raw Tomatoes and Processed Tomato Products." *Appl. Environ. Microbiol.* 57:1367–1371.

Blostein, J. 1991. "An Outbreak Of Salmonella javiana Associated With Consumption Of Watermelon." *J. Environ. Health* 56:29–31.

Bokkenheuser, V. D., N. J. Richardson, J. H. Bryner, D. J. Roux, A. B. Schutte, H. J. Koornhof, I. Freiman, and E. Hartman. 1979. "Detection Of Enteric Camphylobacteriosis In Children." *J. Clin. Microbiol.* 9:227–232.

Boulos, L., M. Prevost, B. Barbeau, J. Coallier, and R. Desjardins. 1999. "Live/Dead BacLight: Application Of A New Rapid Staining Method For Direct Enumeration Of Viable and Total Bacteria In Drinking Water." *J. Microbiol. Methods* 37:77–86.

Braux, A. S., J. Minet, Z. Tamanai–Shacoori, G. Riou, and M. Cormier. 1997. "Direct Enumeration Of Injured *Escherichia coli* Cells Harvested Onto Membrane Filters." *J. Microbiol. Methods* 31:1–8.

Bright, N. G., B. Applegate, M. L. Eldridge, G. S. Sayler, and W. W. Wilhelm. 2000. "Development Of A Bioluminescent Reporter For The Determination Of Aqueous Iron Bioavailability." Presented At The *American Society For Microbiology Annual Meeting*, Los Angeles, CA.

Carriere, C., P. F. Riska, O. Zimhony, J. Kriakov, S. Bardarov, J. Burns, J. Chan, and W. R. Jacobs. 1997. "Conditionally Replicating Luciferase Reporter Phages: Improved Sensitivity For Rapid Detection and Assessment Of Drug Susceptibility Of *Mycobacterium tuberculosis*." *Journal Of Clinical Microbiology* 35:3232–3239.

Chen, J., and M. W. Griffiths. 1996. "Salmonella Detection In Eggs Using Lux$^+$ Bacteriophages." *J. Food Protection* 59:908–914.

Chen, S., A. Yee, M. W. Griffiths, C. Larkin, C. T. Yamashiro, R. Behari, C. Paszko Kolva, K. Rahn, and S. A. De Grandis. 1997. "The Evaluation Of A Fluorogenic Polymerase Chain Reaction Assay For The Detection Of Salmonella Species In Food Commodities." *J. Food Microbiol.* 35:239–250.

Cook, K. L., and J. L. Garland. 1997. "The Relationship Between Electron Transport Activity As Measured By CTC Reduction and CO2 Production In Mixed Microbial Communities." *Microbiol. Ecol.* 34:237–247.

De Lorenzo, V., S. Fernandez, M. Herrero, U. Jakubzik, and K. N. Timmis. 1993. "Engineering Of Alkyl– and Haloaromatic–Responsive Gene Expression With Mini–Transposons Containing Regulated Promoters Of Biodegradative Pathways Of Pseudomonas." *Gene* 130:41–46.

De Lorenzo, V., M. Herrero, U. Jakubzik, and K. N. Timmis. (Nov. 1990.) "Mini–Tn5 Transposon Derivatives For Insertion Mutagenesis, Promoter Probing, and Chromosomal Insertion Of Cloned DNA In Gram–Negative Eubacteria." *J. Bacteriol.* 172:6568–6572.

Del Rosario, B. A., and L. R. Beuchat. (Jan. 1995.) "Survival and Growth Of Enterohemorrhagic *Escherichia coli* 0157:H7 In Cantaloupe and Watermelon." *J. Food Protect.* 58:105–107.

Don, R. H., P. T. Cox, B. J. Wainwright, K. Baker, and J. S. Mattick. 1991. "'Touchdown'PCR To Circumvent Spurious Priming During Gene Amplification." *Nuc. Acids Res.* 19:4008.

Donegan, K., C. Matyac, R. Seidler, and L. A. Porteous. (Jan. 1991.) "Evaluation Of Methods For Sampling, Recovery, and Enumeration Of Bacteria To The Phylloplane." *Appl. Environ. Microbiol.* 57:51–56.

Engelbrecht, J., K. Nealson, and M. Silverman. (Mar. 1983.) "Bacterial Bioluminescence: Isolation and Genetic Analysis Of Functions From Vibrio fischeri." *Cell* 32:773–781.

Frost, J. A., J. M. Kramer, and S. A. Gillanders. 1999. "Phage Typing Of Campylobacter jejuni and Campylobacter coli and Its Use As An Adjunct To Serotyping." *Epidemiol. Infect.* 123:47–55.

Harris, N. V., T. Kimball, N. S. Weiss, and C. Nolan. (May 1986.) "Dairy Products, Produce, and Other Non–Meat Foods As Possible Sources Of Campylobacter Jejuni and Campylobacter coli enteritis." *J. Food Protect.* 49:347–351.

Hay, A. G., B. M. Applegate, N. G. Bright, and G. S. Sayler. 2000. "A Bioluminescent Whole–Cell Reporter For Detection Of 2,4–Dichlorophenoxyacetic Acid and 2,4–Dichlorophenol In Soil." *Applied and Environmental Microbiology* 66:4589–4594.

Hayashi, T. 1981. "Fundamental Studies On The Bacteriophages For Typing *Pseudomonas aeruginosa* and Their Propagating Strains." *Tropical Medicine* 23:119–134.

Hedberg, C. W., K. L. Macdonald, and M. T. Osterholm. (May 1994.) "Changing Epidemiology Of Foodborne Disease: A Minnesota Perspective." *Clinical Infectious Diseases* 18:671–682.

Heid, C. A., J. Stevens, K. J. Livak, and P. M. Williams. 1996. "Real Time Quantitative PCR." *Genome Res.* 6:986–994.

Heitzer, A., K. Malachowsky, J. E. Thonnard, P. R. Bienkowski, D. C. White, and G. S. Sayler. 1994. "Optical Biosensor For Environmental On–Line Monitoring Of Naphthalene and Salicylate Bioavailability With An Immobilized Bioluminescent Catabolic Reporter Bacterium." *Appl. Environ. Microbiol.* 60:1487–1494.

Heitzer, A., O. F. Webb, J. E. Thonnard, and G. S. Sayler. (Jun. 1992.) "Specific and Quantitative Assessment Of Naphthalene and Salicylate Bioavailability By Using A Bioluminescent Catabolic Reporter Bacterium." *Appl. Environ. Microbiol.* 58:1839–1846.

Hellingwerf, K. J., W. C. Crielaard, M. J. T. De Mattos, W. D. Hoff, R. Kort, D. T. Verhammed, and C. Avignone–Rossa. 1998. "Current Topics In Signal Transduction In Bacteria." *Antonie Van Leeuwenhoek* 74:211–227.

Hobbie, J. E., R. J. Daley, and S. Jasper. (May 1977.) "Use Of Nucleopore Filters For Counting Bacteria By Fluorescence Microscopy." *Appl. Environ. Microbiol.* 33:1225–1228.

Jacques, M.A., and C. E. Morris. 1995. "A Review Of Issues Related To The Quantification Of Bacteria From The Phyllosphere." *FEMS Microbiol. Ecol.* 18:1–14.

Khakhria, R., D. Duck, and H. Lior. 1990. "Extended Phage–Typing Scheme For *Escherichia coli* O157:H7." *Epidemiol. Infect.* 105:511–520.

Kimura, B., S. Kawasaki, T. Fuji, J. Kusunoki, T. Itoh, and S. J. A. Flood. 1999. "Evaluation Of Taqman PCR Assay For Detecting Salmonella In Raw Meat and Shrimp." *J. Food Protect.* 62:329–335.

King, J. M. H., P. M. Digrazia, B. Applegate, R. Burlage, J. Sanseverino, P. Dunbar, F. Larimer, and G. S. Sayler. (Aug. 1990.) "Rapid, Sensitive Bioluminescence Reporter Technology For Naphthalene Exposure and Biodegradation." *Science* 249:778–781.

Kodikara, C. P., H. H. Crew, and G. S. A. B. Stewart. 1991. "Near On–Line Detection Of Enteric Bacteria Using Lux Recombinant Bacteriophage." *FEMS Microbiol. Lett.* 83:261–266.

Kudva, I. T., S. Jelacic, P. I. Tarr, P. Youderian, and C. J. Hovde. (Sep. 1999.) "Biocontrol Of *Escherichia coli* O157 With O157–Specific Bacteriophages." *Appl. Environ. Microbiol.* 65:3767–3773.

Layton, A. C., M. Muccini, M. M. Ghosh, and G. S. Sayler. (Dec. 1998.) "Construction Of A Bioluminescent Reporter Strain To Detect Polychlorinated Biphenyls." *Appl. Environ. Microbiol.* 64:5023–5026.

Loessner, M. J., S. Gaeng, G. Wendlinger, S. K. Maier, and S. Scherer. 1998. "The Two–Component Lysis System Of *Staphylococcus aureus* Bacteriophage Twort: A Large TTG–Start Holin and An Associated Amidase Endolysin." *FEMS Microbiology Letters* 162:265–274.

Loessner, M. J., R. B. Inman, P. Lauer, and R. Calendar. 2000. "Complete Nucleotide Sequence, Molecular Analysis and Genome Structure Of Bacteriophage A118 Of Listeria monocytogenes: Implications For Phage Evolution." *Mol. Microbiol.* 35:324–340.

Loessner, M. J., C. E. D. Rees, G. S. A. B. Stewart, and S. Scherer. (Apr. 1996.) "Construction Of Luciferase Reporter Bacteriophage A511::LuxAB For Rapid and Sensitive Detection Of Viable Listeria Cells." *Appl. Environ. Microbiol.* 62:1133–1140.

Lyngberg, O. K., D. J. Stemke, J. L. Schottel, and M. C. Flickinger. 1999. "A Single–Use Luciferase–Based Mercury Biosensor Using *Escherichia coli* HB101 Immobilized In A Latex Copolymer Film." *Journal Of Industrial Micribiology & Biotechnology* 23(1):668–676.

Mackowiak, C. L., G. W. Stutte, R. M. Wheeler, L. M. Ruffe, and N. C. Yorio. 1999. "Tomato and Soybean Production On A Shared Recirculating Hydroponic System." *Acta Horticulturae* 481:259–266.

Madou, M. J., Y. Lu, S. Lai, C. G. Koh, L. J. Lee, and B. R. Wenner. 2001. "A Novel Design On A CD Disc For 2–Point Calibration Measurement." *Sensors Actuators A* 91:301–306.

Mahon, B. E., A. Ponka, W. N. Hall, K. Komatsu, S. E. Dietrich, A. Siitonen, G. Cage, P. S. Hayes, M. A. Lambert-Fair, N. H. Bean, P. M. Griffin, and L Slutsker. (Apr. 1997.) "An International Outbreak Of Salmonella Infections Caused By Alfalfa Sprouts Grown From Contaminated Seeds." *J. Infect. Dis.* 175:876–882.

Marks, T., and R. Sharp. 2000. "Bacteriophages and Biotechnology: A Review." *J. Chem. Technol. Biotechnol.* 75:6–17.

Marsh, P., N. Z. Morris, and E. M. H. Wellington. 1998. "Quantitative Molecular Detection Of *Salmonella typhimurium* In Soil and Demonstration Of Persistence Of An Active But Non–Culturable Population." *FEMS Microbiol. Ecol.* 27:351–363.

Mead, P. S., L. S. Slutsker, V. Dietz, L. F. McCaig, J. S. Bresse, C. Shapiro, P. M. Griffin, and R. V. Tauxe. 1999. "Food–Related Illness and Death In The United States." *Emerging Infectious Diseases* 5:607–625.

Meighen, E. A. (Mar. 1991.) "Molecular Biology Of Bacterial Bioluminescence." *Microbiol. Rev.* 55:123–142.

Miller, R. V., J. M. Pemberton, and K. E. Richards. 1974. "F116, D3, and G101: Temperate Bacteriophages Of *Pseudomonas aeruginosa.*" *Virology* 59:566–569.

Morita, R. Y. 1982. "Starvation–Survival Of Heterotrophs In The Marine Environment." *Adv. Microb. Ecol.* 6:171–198.

Norton, D. M., and C. A. Batt. (May 1999.) "Detection Of Viable Listeria monocytogenes With A 5' Nuclease PCR Assay." *Appl. Environ. Microbiol.* 65:2122–2127.

Oberst, R. D., M. P. Hays, L. K. Bohra, R. K. Phebus, C., T. Yamashiro, C. Paszko–Kolva, S. J. A. Flood, J. M. Sargeant, and J. R. Gillespie. (Sep. 1998.) "PCR–Based DNA Amplification and Presumptive Detection Of *Escherichia coli* O157:H7 With An Internal Fluorogenic Probe and The 5' Nuclease (TaqMan) Assay." *Appl. Environ. Microbiol.* 64:3389–3396.

Pagotto, F., L. Brovko, and M. W. Griffiths. 1996. "Phage-Mediated Detection Of Staphylococcus aureus and *Escherichia coli* Using Bioluminescence." *Bacteriological Quality Of Raw Milk* 9601:152–156.

Riess, A. A., S. Zaza, C. Langkop, R. V. Tauxe, and P. A. Balke. 1990. "A Multistate Outbreak Of *Salmonella chester* Linked To Imported Cantaloupe." *Presented At The Interscience Conference On Antimicrobial Agents and Chemotherapy,* Washington, D.C.

Ripp, S. B. Applegate, N. G. Bright, R. Stapleton, and G. S. Sayler. 1999a. "On–Site Field Analysis Of Groundwater Contaminants Utilizing Bioluminescent Bioreporter Microorganisms," *American Society For Microbiology Annual Meeting,* Chicago, IL.

Ripp, S., B. Applegate, N. G. Bright, and G. S. Sayler. 2000a. "Whole–Cell Bioluminescent Bioreporters For The Detection Of Biogenic Amines In Food. " Presented At The *American Society For Microbiology Annual Meeting,* Los Angeles, CA.

Ripp, S., D. E. Nivens, Y. Ahn, C. Werner, J. Jarrel, J. P. Easter, C. D. Cox, R. S. Burlage, and G. S. Sayler. 2000b. "Controlled Field Release Of A Bioluminescent Genetically Engineered Microorganism For Bioremediation Process Monitoring and Control." *Environ. Sci. Technol.* 34(5):846–853.

Ripp, S., B. M. Applegate, D. E. Nivens, M. J. Paulus, G. E. Jellison, M. L. Simpson, and G. S. Sayler. 1999b. "Whole-Cell Environmental Monitoring Devices: Bioluminescent Bioreporter Integrated Circuits (BBICs)." In A. Mulchandani and O. A. Sadik (ed.), *Recent Advances In Environmental Chemical Sensors and Biosensors,* vol. In Press, ACS Press, Clarendon Hills, IL.

Sanseverino, J., B. Applegate, H. King, and G. Sayler. 1993. "Plasmid–Mediated Mineralization Of Naphthalene, Phenanthrene, and Anthracene." *Appl. Environ. Microbiol.* 59:1931–1937.

Saylor, G. S., U. Matrubutham, F. M. Menn, W. H. Johnston, and R. D. Stapleton. 1998. "Molecular Probes and Biosensors In Bioremediation and Site Assessment," P. 385–434. In S. K. Sikdar and R. L. Irvine (ed.), *Bioremediation: Principles and Practice,* vol. 1. Technomic Publishing Company, Inc., Lancaster, PN.

Schlech, W. F., P. M. Lavigne, R. A. Bostoulussi, A. C. Allen, E. V. Haldane, A. J. Wort, A. W. Hightower, S. E. Johnson, S. H. King, E. S. Nicholls, and C. V. Broome. 1983. "Epidemic Listeriosis—Evidence For Transmission By Food." *New Eng. J. Med.* 208:203–206.

Simpson, M. L., G. S. Sayler, G. Patterson, D. E. Nivens, E. Bolton, J. Rochelle, C. Arnott, B. Applegate, S. Ripp, and M. A. Guillorn. 2001. "An Integrated CMSO Microluminometer For Low–Level Luminescence Sensing In The Bioluminescent Bioreporter Integrated Circuit." *Sensors Actuators* B 72:134–140.

Simpson, M. L., G. S. Sayler, B. M. Applegate, S. Ripp, D. E. Nivens, M. J. Paulus, and G. E. Jellison. (Aug. 1998.) "Bioluminescent Bioreporter Integrated Circuits Form Novel Whole–Cell Biosensors." *Trends Biotech.* 16:332–338.

Steinbregge, E. G., R. B. Maxcy, and M. B. Liewen. (Aug. 1988.) "Fate Of Listeria monocytogenes On Ready To Serve Lettuce." *J. Food Protect.* 51:596–599.

Stewart, G. S. A. B., S. A. A. Jassim, S. P. Denyer, P. Newby, K. Linley, and V. K. Dhir. 1998. "The Specific and Sensitive Detection Of Bacterial Pathogens within 4 H Using Bacteriophage Amplification." *J. Appl. Microbiol.* 84:777–783.

Stewart, Gordon; Smith, Tony and Denyer, Stephen. 1989. "Genetic Engineering for Bioluminescent Bacteria—Harnessing Molecular Genetics to Provide Revolutionary New Methods for Food Microbiloby." *Food Science & Tech. Today* 3(1): 19–22.

Stewart, P. R., H. G. Waldron, J. S. Lee, and P. R. Matthews. 1985. "Molecular Relationships Among Serogroup B Bacteriophages Of *Staphylococcus aureus.*" *Journal Of Virology* 55:111–116.

Sumner, S. S., and D. L. Peters. 1997. "Microbiology Of Vegetables," P. 87–114. In D. S. Smith, J. N. Cash, W. K. Nip, and Y. H. Hui (ed.), *Processing Vegetables Science and Technology.* Technomic Publishing Co., Lancaster, PA.

Tauxe, R. V. 1992. "Epidemiology Of Campylobacter jejuni Infections In The United States and Other Industrialized Countries," P. 9–19. In I. Nachamkin, M. J. Blaser, and L. Tompkins (ed.), "Campylobacter Jejuni: Current Status and Future Trends." *American Society For Microbiology,* Washington D.C.

Ulitzur, S., and J. Kuhn. 1987. "Introduction Of Lux Genes Into Bacteria, A New Approach For Specific Determination Of Bacteria and Their Antibiotic Susceptibility," P. 463–472. In J. Scholmerich, R. andreesen, A. Kapp, M. Ernst, and W. G. Woods (ed.), *Bioluminescence and Chemiluminescence: New Perspectives.* John Wiley & Sons, New York.

Van Der Mee–Marquet, N., M. Loessner, and A. Audurier. (Sep. 1997.) "Evaluation Of Seven Experimental Phages For Inclusion In The International Phage Set For The Epidemiological Typing Of Listeria monocytogenes." *Appl. Environ. Microbiol.* 63:3374–3377.

Vanne, L., M. Karwoski, S. Karppinen, and A. M. Sjoberg. 1996. "HACCP–Based Food Quality Control and Rapid Detection Methods For Microorganisms." *Food Control* 7:263–276.

Waddell, T. E., and C. Poppe. 1999. "Construction Of Mini–Tn10luxABcam/Ptac–ATS and Its Use For Developing A Bacteriophage That Transduces Bioluminescence To *Escherichia coli* O157:H7." *FEMS Microbiol. Ecol.* 182:285–289.

Wheeler, R. M., C. L. Mackowiak, J. C. Sager, N. C. Yorio, and W. M. Knott. 1994. "Growth and Gas Exchange Of Lettuce Stands In A Closed, Controlled Environment." J. *American Soc. Hort. Sci.* 119:610–615.

Winson, M. K., S. Swift, L. Fish, J. P. Throup, F. Jorgensen, S. R. Chhabra, B. W. Bycroft, P. Williams, and G. S. A. B. Stewart. 1998. "Construction and Analysis Of LuxCDABE–Based Plasmid Sensors For Investigating N–Acyl Homoserine Lactone–Mediated Quorum Sensing." *FEMS Microbiol. Lett.* 163:185–192.

Winters, D. K., A. E. O'Leary, and M. F. Slavik. 1998. "Polymerase Chain Reaction For Rapid Detection Of Campylobacter jejuni In Artificially Contaminated Foods." *Lett. Appl. Microbiol.* 27:163–167.

Winters, D. K., and M. F. Slavik. 2000. "Multiplex PCR Detection Of Campylobacter jejuni and Arcobacter butzleri In Food Products." *Mol. Cell Probes* 14:95–99.

Wood, R. C., C. Hedberg, and K. White. 1991. "A Multistate Outbreak Of *Salmonella javian* Infections Associated With Raw Tomatoes." Presented At The *CDC Epidemic Intelligence Service, 40th Annual Conference,* Atlanta, GA.

Zepeda–Lopez, H., M. Ortega–Rodriquez, E. I. Quinonez–Ramirez, and C. Vazguez–Salinas. 1995. "Isolation Of *Escherichia coli* O157:H7 From Vegetables." *Presented At The American Society For Microbiology Annual Meeting,* Washington, D.C.

Zhuang, R. Y., L. R. Beuchat, and F. J. Angulo. (Jun. 1995.) "Fate Of Salmonella montevideo In Raw Tomatoes As Affected By Temperature and Treatment With Chlorine." *Appl. Environ. Microbiol.* 61:2127–2131.

* cited by examiner

BIOLUMINESCENT BIOSENSOR DEVICE

1.0 BACKGROUND OF THE INVENTION

1.1 Field of The Invention

The invention pertains to methods and devices for detecting targeted microorganisms such as bacteria by inducing bioluminescence in bioreporter cells. Genetically engineered bacteriophage are employed to infect target bacteria in the presence of genetically engineered bioreporter cells. The bioreporter cells respond by producing light upon stimulation by an inducer. The inducer is produced as a result of infection of the target bacteria by the bacteriophage.

1.2 Description of the Related Art

Current technology focusing on the development of biologically-based detection systems has prompted efforts to address the need for methods for detecting specific microbial pathogens. Numerous methods for determining the presence of microbial contaminants have been used over the years; typically, culture methods were employed in the past but these methods were slow and inefficient. Recent developments in bioreporter technology have prompted use of genetically engineered bacteria or bacteriophage to identify toxic chemical compounds, and, in some cases, to identify particular species of bacteria.

Bioreporters are genetically engineered organisms designed to detect specific compounds by incorporating a gene responsive to a selected external compound, for example by using a heterologous promoter responsive to a target compound where the promoter then induces expression of a detectable gene product in the bioreporter cell. Bioluminescent bioreporters, as used in the present context, are genetically engineered bacteria incorporating genes that when expressed result in bioluminescence. Upon detection of a specific compound, the bioreporter cell responds by producing light. A popular gene for this purpose is the lux gene. Under proper conditions, the lux genes are expressed and the subsequent bioluminescence is detectable by any of a variety of optical methods. Many of the constructs incorporated in bioluminescent bioreporter organisms derive from the bioluminescent marine bacterium *Vibrio fischeri* (King et al., 1990).

Sayler et al. (1998) have described bioluminescent bacterial-based bioreporters that respond to specific compounds via the production of visible light. A variety of lux-based bacterial bioreporters has been used to detect and monitor naphthalene (Heitzer et al., 1994), BTEX (benzene, toluene, ethylbenzene, and xylene) (Applegate et al., 1998), polychlorinated biphenyls (PCBs) (Layton et al., 1998), 2,4-dichlorophenoxyacetic acid (2,4-D) (Hay et al,. 2000), ammonia (Simpson et al., 2001), and the food spoilage indicator chemical β-phenylethylamine (Ripp et al., 2000a).

Genetic constructs for imparting bioluminescence to bacterial bioreporter cells have generally employed a lux gene cassette derived from the marine bacterium *Vibrio fischeri* (Engebrecht, et al., 1983). As used herein, "cassette" refers to a recombinant DNA construct made from a vector and inserted DNA sequences. The complete lux cassette consists of five genes, i.e. luxA, B, C, D and E. LuxA and luxB encode the proteins that are responsible for generating bioluminescence while luxC and D encode an aldehyde required for the bioluminescence reaction.

The light response generated by bioluminescent bioreporters is typically measured with optical transducers such as photomultiplier tubes, photodiodes, microchannel plates, or charge-coupled devices. Some means of transferring the bioluminescent signal to the transducer is required, which necessitates the need for fiber optic cables, lenses or liquid light guides. Such instruments are generally unsuitable for field use. What typically results is a large, bulky instrument anchored to power and optic cables. For example, in field release experiments described by Ripp et al. (2000b), a bioluminescent bioreporter for the detection of naphthalene was used for monitoring of polyaromatic hydrocarbon degradation in soil. Bioluminescent signals were detected using a multiplexed photomultiplier tube linked to a network of fiber optic cables that proved to be expensive, fragile, and cumbersome to work with.

Battery-operated, hand-held photomultiplier units that may be interfaced with a laptop computer have been described and used in conjunction with bioreporters for field analysis of hydrocarbon contamination in groundwater (Ripp, et al., 1999a). Special bioluminescent bioreporter integrated circuits (BBICs) have been reported (Simpson, et al., 2001) and these self contained units have been shown to detect environmental contaminants such as naphthalene and BTEX by simply exposing the BBIC device to samples containing these compounds (Ripp et al, 1999b). The bioluminescent bioreporters utilized in these devices are genetically modified bacterial bioreporters that respond to specific chemicals in the environment via production of visible light.

Detection of pathogenic organisms, as opposed to chemical agents, is another area of current interest. Pathogens such as those causing human and animal diseases, foodborne pathogens and those used in biological warfare are of great significance for the safety of human populations. Furthermore, the continual appearance of new strains of bacteria underscores the need for sophisticated detection systems.

In the food industry as an example, microbial contamination of fresh fruits and vegetables has become a mounting concern during the last decade due to an increased emphasis of these products in a healthy diet and the recognition of new foodborne pathogens such as *Campylobacter jejuni*, *Escherychia coli* O157:H7, and *Listeria monocytogenes* (Tauxe, 1992). Federal agencies have published recommended safe food handling practices for minimizing risk; however rapid, real-time methods for detection of pathogens in the production, processing, and distribution systems are not yet available. Of particular concern in monitoring food safety is the need to identify the bacteria that cause the majority of food-related deaths in the United States, including Salmonella, *Listeria monocytogenes, Escherychia coli* O157:H7 and Campylobacter.

Bioluminescent methods to determine bacterial contamination are currently in use in the food industry. One technology, based on detection of ATP, relies on the biochemical requirement of all bacteria to utilize ATP for the energy production that is necessary for survival and growth. Unfortunately the ATP detection method is non-specific in nature; thus it does not differentiate among bacterial species nor does it distinguish non-pathogenic bacteria from pathogens that pose significant health risks (Vanne, et al., 1996).

Several reports have documented bioluminescent detection of a target bacterium using bacteriophage infection. Table 1 summarizes select pathogens that have been detected by these procedures.

TABLE 1

Bioluminescence detection of bacterial pathogens by bacteriophage containing a luxAB insert.

| Pathogen | Bacteriophage | Detection Limit | Test Source | Reference |
|---|---|---|---|---|
| Enterobacteriaceae | Unspecified | 10 cells/g/cm$^2$ | Surface and meat carcass swabs | Kodikara et al., 1991 |
| Escherichia coli species | λ Charon | 100 cells/ml | Milk | Ulitzer and Kuhn, 1987 |
| Escherichia coli O157:H7 | φ V10 | Not determined | Pure culture | Waddell and Poppe, 1999 |
| Listeria monocytogenes | A511 | 10 cells/g | Cheese, pudding, cabbage | Loessner et al., 1996 |
| Salmonella species | P22 | 10 cfu/ml | Eggs | Chen and Griffiths, 1996 |
| Salmonella typhimurium | P22 | 100 cells/ml | Pure culture | Stewart et al., 1989 |
| Staphylococcus aureus | Unspecified | 1000 cfu/ml | Pure culture | Pagotto et al., 1996 |

In all of these cases, the bacteriophage contained only an incomplete lux gene, i.e. luxAB. While useful in detection of some pathogenic species, the technique suffers from several disadvantages. When only the luxAB genes are employed, an exogenous source of the aldehyde substrate for the luciferase reaction is required for detection of the bioluminescent response. This can raise problems with detection. Moreover, there are further difficulties because conditions such as the amount of added inducer may have to be adjusted. This is particularly inconvenient if the methods are used in situations such as on farms where the environment may not be conducive to running the assays and the end-user is not likely to be highly trained.

A further problem associated with bacterial detection is that often pathogens are present in very low concentrations. In such cases, existing bioluminescent methods may suffer from the disadvantage that the amount of light produced is too low to be detectable. To overcome problems of detection associated with low bacterial concentration, several non-bioluminescent detection methods are in current use. These methods often incorporate amplification procedures, such as sample pre-enrichment steps in order to elevate pathogen concentrations to detectable levels, or DNA-based polymerase chain reaction (PCR) amplification techniques. The disadvantage of these amplification steps is that they require extensive user training and expensive instrumentation.

There is therefore a need for the development of methods and devices for detecting specific bacteria, particularly pathogens, selectively, quickly, accurately and with high sensitivity. New devices are needed to provide accurate and sensitive monitoring of a variety of common pathogens, such as those implicated in health hazards associated with food and food processing, hospital environments and biological warfare.

2.0 SUMMARY OF THE INVENTION

The present invention addresses some of the deficiencies in the methods and devices presently employed in detecting individual species of bacteria, by providing a novel internally amplified bioluminescent bacteriophage/bioreporter system. In particular, the disclosed devices enable rapid and sensitive detection of specific pathogens by means of a simple-to-use fully integrated system requiring nothing more than sample addition. The sensitivity of the device is achieved by a signal amplification mechanism integrated into the design. The invention includes two cooperating elements, i.e. biosensor and bioreporter elements, that combine to operate through a novel two-step process. Biosensor elements of the invention are exemplified by genetically modified bacteriophage while the bioreporter elements may be any of a number of genetically modified cell lines. A selected pathogen, e.g., a bacterium, is infected with the biosensor bacteriophage; as a result of the infection, the bacterium produces an inducer that causes the bioreporter cell line to express the lux gene cassette, resulting in amplified bioluminescence that is readily detectable.

In particular embodiments, the invention employs bacteriophage genetically modified to carry a luxI gene. The luxI gene encodes a protein product, acyl homoserine lactone synthetase which carries out a condensation reaction of cell metabolites resulting in the production of acyl en homoserine lactone N-(3-oxohexanoyl) homoserine lactone (AHL). A selected target bacterium is infected with the genetically modified bacteriophage. Upon infection, the phage luxI gene is transcribed in the bacterium, with resultant expression of the LuxI protein by the infected target cell. AHL molecules produced in the target cell diffuse out of the target into the surrounding medium.

In the invention, infection of the target bacteria takes place in the proximity of bioreporter cells, which are genetically engineered to produce light upon stimulation by AHL. In the absence of the AHL inducer, the bioreporter cells produce little or no light. However, when the target bacteria release AHL following phage infection, AHL molecules are taken up from the surrounding medium by the bioreporter cells, and this uptake induces production of bioluminescent proteins in the bioreporter cells. This occurs because the bioreporter cell is genetically engineered to include a lux gene cassette (luxR+luxI+luxCDABE) that is responsive to AHL. AHL is an autoinducer that positively regulates the lux operon. Thus, upon stimulation with an AHL complex, the lux genes in the bioreporter cells are induced, resulting in the production of light.

A unique aspect of the invention is the amplification of bioluminescence due to the presence of the lux-modified bioreporter cells. Induction of the lux genes in one bioreporter cell results not only in the production of light-producing proteins, but also of AHL molecules. These AHL molecules then diffuse out of the light-producing bioreporter cells and further induce expression of the lux genes in neighboring bioreporter cells. This cascade effect, involving multiple neighboring bioreporter cells, results in intense bioluminescence. The infection of a target bacterium thus results in a chain reaction of bioluminescence in multiple bioreporter cells. This enables detection of very low levels of target bacteria. This novel integrative approach enables rapid pathogen detection without sample enrichment.

The bacteriophage/bioreporter system employs a luxI-integrated bacteriophage that infects only a particular bacterium. In the practice of the invention, one first selects a target bacterium, identifies a bacteriophage specific for the target bacterium and genetically engineers the bacteriophage to incorporate the luxI gene. The specificity of phage infection can be utilized to identify, detect or monitor select species of bacteria.

In most real-life situations, the target bacteria are in a natural environment, often in the presence of other microbes and various contaminants. The bacteriophage/bioreporter system addresses this problem by directing the luxI bacteriophage against specific strains of bacteria. Target bacteria may be selected from a wide variety of commonly known pathogens. Of particular interest are several types of bacteria often associated with food contamination; these include Salmonella, *Escherychia coli* species such as O157:H7, *Listeria monocytogenes*, enterobacteriaceae, as well as persistent infectious microorganisms such as *Bacillus anthracis, Staphylococcus aureus* and *Yersinia pestis*.

Numerous other bacteria may be readily detected using the disclosed methods and devices provided that appropriate infectious phage may be identified or engineered. In practice, identification of pathogen depends on first identifying a pathogen-specific bacteriophage. Many are known; for example, bacteriophage M13 that infects *E. coli*. Further examples of bacteriophage that specifically infect pathogenic bacterial species are listed in Table 4.

A major consideration is the identification and genetic alteration of a species-specific bacteriophage to harbor the luxI cassette and to efficiently penetrate the bacterial cell so that the luxI can be successfully expressed in the target bacterium. A particular example is the use of bacteriophage M13 to infect *E. coli*.

Certain embodiments of the invention encompass simultaneously contacting a sample with multiple bacteriophage biosensors, each of which specifically recognizes a particular bacterium and is contained within a separate sample compartment. In this way, multiple target cells of select types may be detected simultanously. The bacteriophage/bioreporter elements can be integrated onto a chip surface to provide a convenient, easily handled device.

Some embodiments of the invention encompass multicomponent packaged kits containing both sensor and detector elements for detection of one or more select strains of bacteria. For sensing of select bacterial targets in a sample suspected of bacterial presence, such kits contain one or more types of genetically engineered bacteriophage, each designed to specifically infect a selected bacterium, and upon infection, to cause expression of an inducer molecule by the selected bacterium. In particular embodiments, the bacteriophage contain a luxI gene, the product of which results in formation of AHL, an inducer of the lux genes in lux-based bioluminescent cells. For detection of the infected bacterium, the kits contain a population of genetically engineered bacterial bioreporter cells capable of bioluminescence when stimulated by the inducer. In particular embodiments, the bioreporter bacteria contain a luxR-lux$_{pro}$/lux I/luxCDABE gene, which is induced to produce light when stimulated by AHL. Kits may further include instructions for use, and optionally a device for measurement of the generated light, such as an integrated circuit adapted for detecting a bioluminescent signal. The integrated circuit may comprise a photodetector, low noise electronics (e.g. on-chip wireless communication system), biocompatible housing, and a semi-permeable membrane covering the bioreporter region.

The disclosed methods and devices derive from biologically-based sensor technology that can be readily adapted to pathogen detection and quality control programs. Since the required elements of the system—biosensors and autoamplifying bioluminescent bioreporters—are completely integrated within compartments of the detector device, this system has the advantage of extreme ease of use. Operation of the system entails simply contacting a sample with a sample chamber of the device and allowing the device to process the ensuing bioluminescent signal and communicate the results. The application of this technology to important issues such as food safety and hygienic quality represents a novel method for detecting, monitoring, and preventing biological contamination.

3.0 BRIEF DESCRIPTION OF THE DRAWINGS

FIG. 1. schematically illustrates the lux-based mechanism of bioluminescent light generation of *Vibrio fischeri*.

Figure 2:
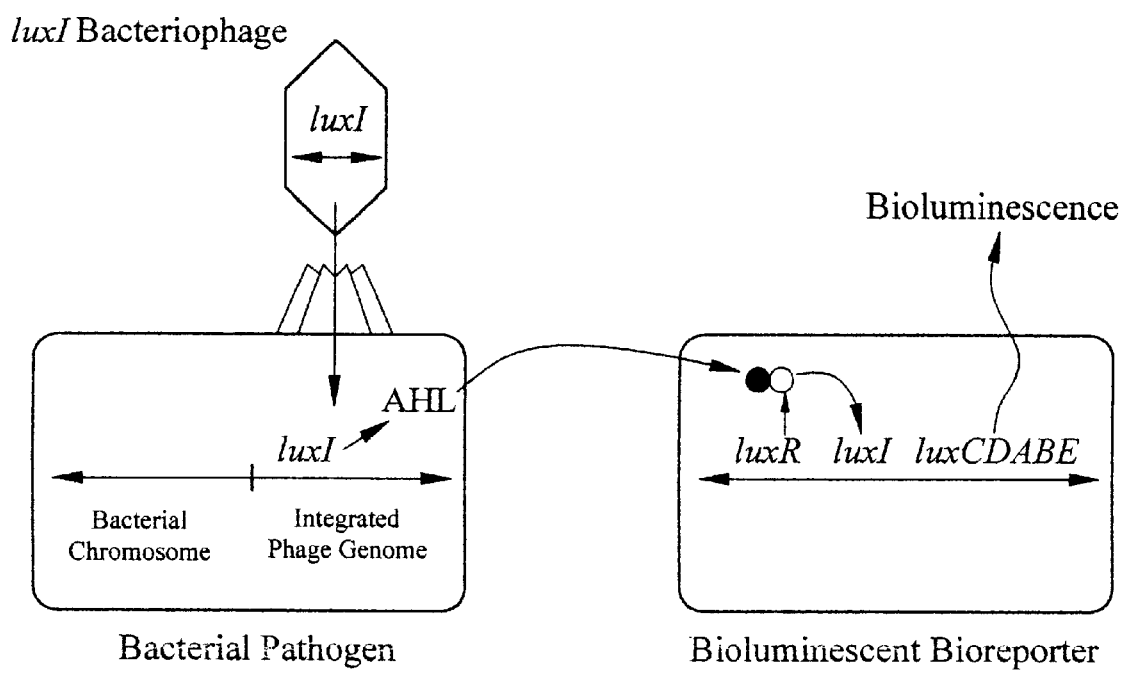

FIG. 2. shows the scheme for detection of specific bacterial pathogens using luxI bacteriophage and bioluminescent bioreporter cells containing the luxR/luxI/luxCDABE gene cassette.

Figure 3:
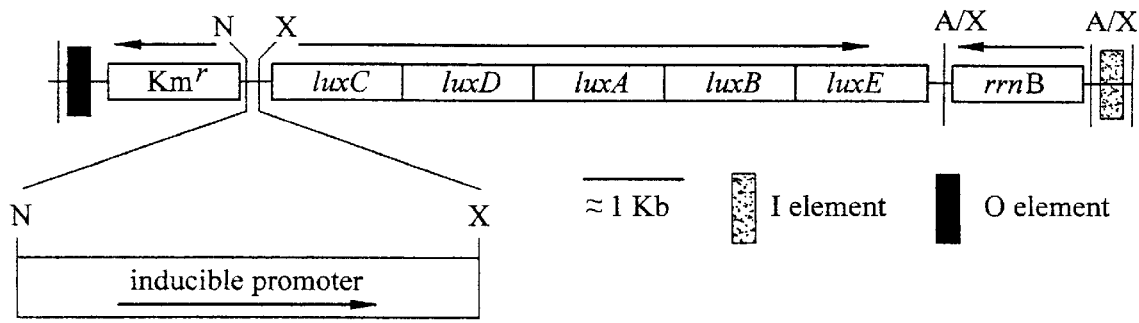

FIG. 3. shows a schematic representation of the Mini-Tn5 acyl-homoserine lactone (AHL)-regulated lux transcriptional fusion.

Figure 4:
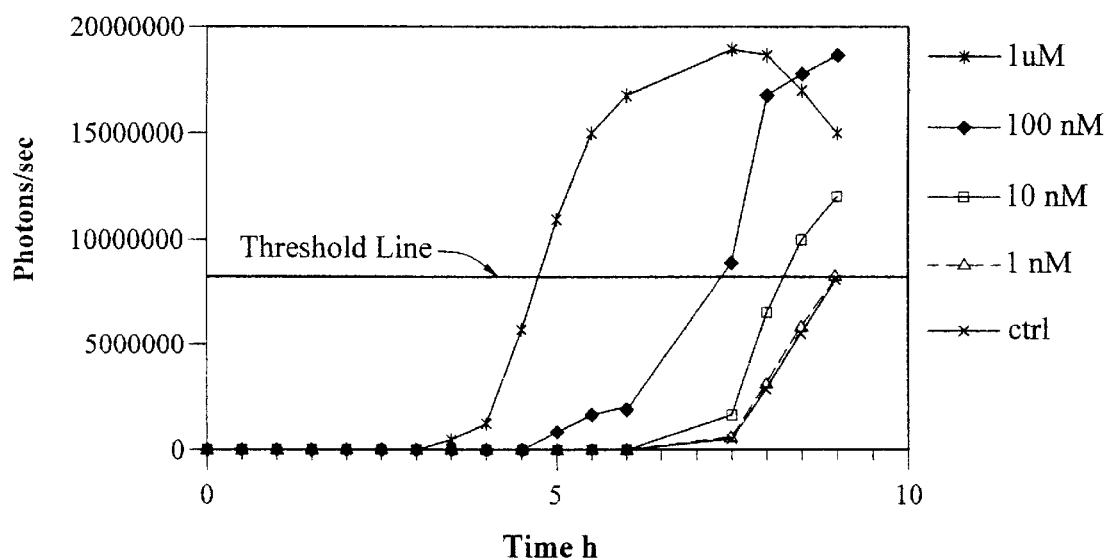

FIG. 4. shows that bioluminescence in *V. fischeri* increases in proportion to the initial concentration of inducer in the culture media.

Figure 5:
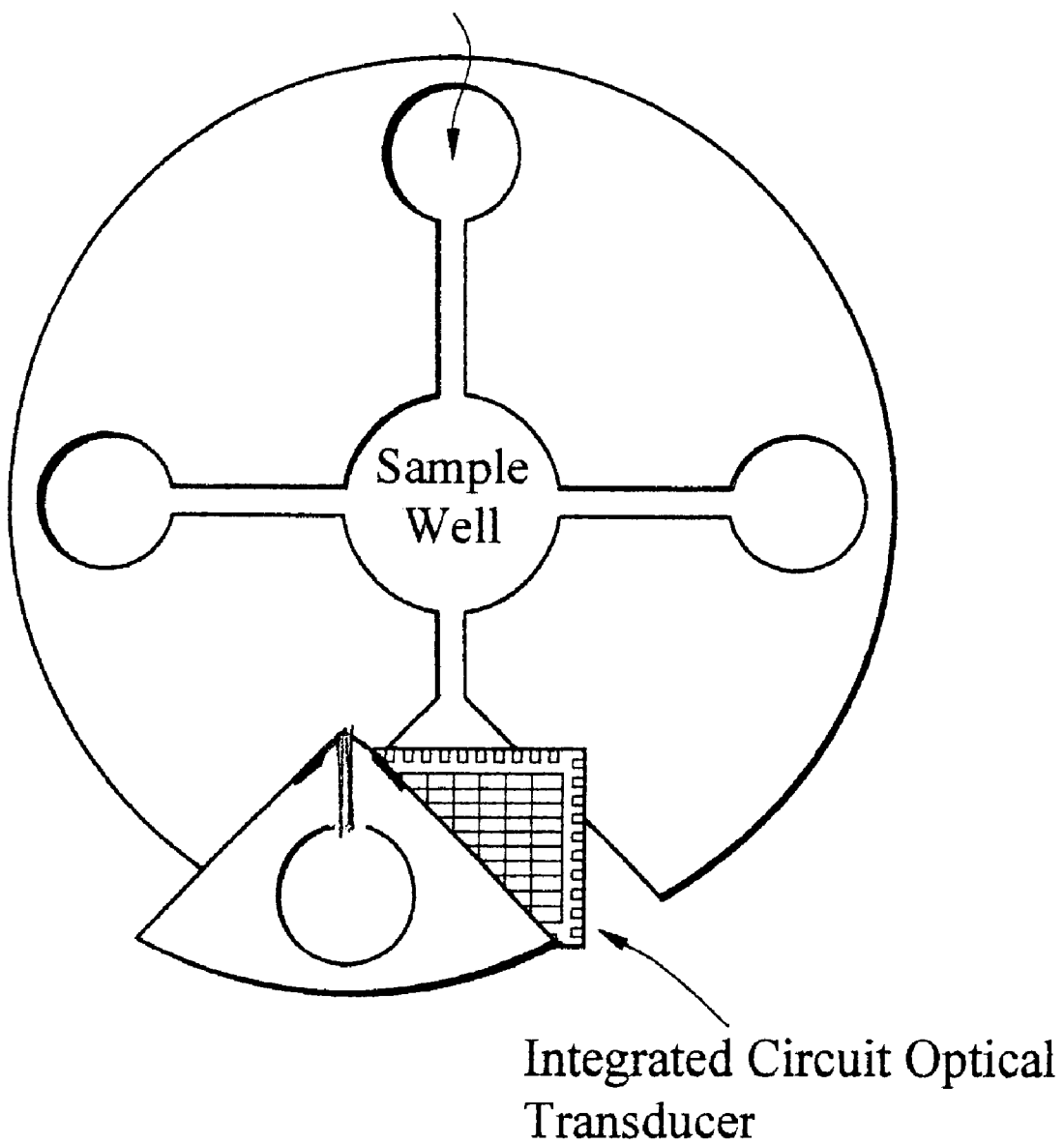

FIG. 5. shows a bacteriophage/bioluminescent bioreporter system and integrated circuit optical transducer embedded in a compact disk (CD) format. The CD is designed with wells that contain a luxI bacteriophage biosensor specific for a select bacterial pathogen, as well as bioluminescent bioreporter cells engineered to respond to the luxI AHL gene product. The sample to be tested is placed within a central well of the compact disk. Spinning the disk distributes the sample to the outer wells. If the target pathogen is present in the sample, infection by the bacteriophage occurs, AHL is released from the infected target cells, and subsequent bioluminescent signals are generated by the bioreporter cells and detected by an embedded integrated circuit optical transducer.

4.0 DETAILED DESCRIPTION OF THE PREFERRED EMBODIMENTS

4.1 *Vibrio Fischeri* Bioluminescence

The invention utilizes genetically engineered bioluminescent bioreporter cells. The capacity of these cells to produce light is due to incorporation of the lux genes, which are responsible for bioluminescence in the marine bacterium

*Vibrio fischeri*. FIG. 1 is a schematic representation of the lux genes, showing positive regulation of these genes by the luxI and luxR gene products. The luciferase genes (luxAB) encode proteins responsible for generating bioluminescence while the reductase (luxC), transferase (luxD), and synthetase (luxE) genes code for proteins involved in producing an aldehyde substrate required in the bioluminescent reaction. In FIG. 1, the gene sequences are represented by open boxes. The small circles represent the expressed regulatory elements of the luxR and luxI genes. The expressed product of the luxI gene is acyl-homoserine lactone (AHL) synthetase. Its product, acyl homoserine lactone (AHL), acts as an inducer of the bioluminescent reaction. AHL, represented by black circles, forms a complex with the expressed product of the luxR gene, i.e. LuxR transcriptional regulator (white circles). This complex (black and white circles) binds to the promoter site of the luxI gene (black box). Transcription is induced, in the direction of the lower arrow, of luxI and luxCDABE, which code for the proteins that carry out the biochemical reactions resulting in the production of 490 nm light. This mechanism of positive regulation of the lux operon by the LuxR-AHL complex occurs both in native *Vibrio fischeri* and in the recombinantly introduced lux gene cassette in the bioreporter cells.

Light generation in Vibrio and in the bioreporter cells is amplified by a mechanism known as autoinduction. The luxI gene results in production of AHL, which diffuses into the extracellular environment where at a threshold concentration it induces luxI and luxCDABE transcription of neighboring bioluminescent cells and itself, in a cascade effect that ultimately generates intense bioluminescence from the group of cells. The effect of the autoinduction mechanism is to amplify significantly the production of light, by engaging a large number of cells in the effort. The present invention utilizes autoinduction to amplify the production of light by genetically engineered lux-based bioluminescent bioreporter cells.

4.2 Bioluminescent Bioreporter System

As seen in FIG. 2, the invention utilizes two elements, i.e. a biosensor and a bioreporter. The purpose of the biosensor is twofold—1) to sense, or detect the presence of a target cell such as a bacterium and attach to it; and 2) to transfer DNA into the target cell. An exemplary biosensor is a luxI integrated bacteriophage that specifically infects a particular pathogenic strain of bacteria. Infection of the bacterial target with the biosensor DNA causes the target cell to produce gene products encoded by the biosensor DNA. In the case of luxI-integrated bacteriophage, the infected bacterium produces the luxI gene product acyl homoserine lactone synthetase, with ultimate production of AHL.

A second element of the bacteriophage/bioreporter system is the bioreporter cell. The bioreporter also serves two functions—1) to respond to the signal it receives from the biosensor; and 2) to amplify that signal so that multiple bioreporters are in turn responsive to the signal initiated by the infected target cell. The bioreporter is conveniently a bacterial cell line genetically engineered to produce light upon stimulation by the target cell signal. In systems using luxI bacteriophage, that signal is AHL.

FIG. 2 shows a bacteriophage/bioreporter system in which the bacteriophage biosensor incorporates a luxI construct and the bacterial bioreporter cell incorporates the lux R+I+CDABE constructs. The bioreporter element of the invention is able to produce light, without need for addition of exogenous chemicals, by the inclusion of the complete luxCDABE gene cassette. This is due to the fact that the lux operon, both in Vibrio and in the genetically engineered bioreporter cells, is positively regulated by the luxI and luxR genes. (FIG. 1).

Taking advantage of the autoinduction mechanism of *Vibrio fischeri*, amplification of the bioluminescent signal is achieved in the invention through diffusion and uptake of AHL molecules from multiple bioreporter cells placed in close proximity. The AHL released by one cell is taken up from the medium by adjacent cells. This AHL binds to the luxR binding sites in the neighboring cells, causing lux gene transcription initiation from the promotor site ($P_{lux}$) and production of more AHL by these cells. As the concentration of the AHL increases, so does the number of LuxR binding episodes. The resultant involvement of multiple bioluminescing cells creates intense levels of bioluminescence.

4.3 Materials and Methods for Construction of Bacteriophage and Bioreporter Bacterial Cell Lines Plasmids and bacterial strains suitable for practice of the invention are listed in Table 2.

TABLE 2

Plasmids and bacterial strains utilized in bioluminescent bioreporter and luxI bacteriophage construction strategies.

|  | Relevant genotype/characteristics | Reference |
|---|---|---|
| Plasmids |  |  |
| PCR ™II | 3.9 kb cloning vector for PCR products with 3' A overhangs, $Ap^R$, $Km^R$ | Invitrogen Carlsbad, CA. |
| pUTK214 | pUT/mini-Tn5KmNX, $Ap^R$, $Km^R$ | Applegate et al., 1998 |
| pUTK222 | pUT/mini-Tn5KNX-lux containing the promoterless lux gene cassette with unique NotI-XbaI cloning sites for promoter insertion, $Ap^R$, $Km^R$ | Hay et al., 2000 |
| Bacterial Strains |  |  |
| *E. coli* SV17-1(λpir) | λpir, recA, thi, pro, hsdR$^-$M$^+$, RP4:2-Tc:Mu:Km Tn7Tp$^R$Sm$^R$; mobilizing strain for pUT mini-Tn5 derivatives | DeLorenzo et al., 1990, 1993 |

TABLE 2-continued

Plasmids and bacterial strains utilized in bioluminescent bioreporter and luxI bacteriophage construction strategies.

| | Relevant genotype/characteristics | Reference |
|---|---|---|
| E. coli INVαF' | Strain used with TA cloning vector, pCR ™II F' φ80lacZαΔM15 Δ(lacZYA-argF)U169 deoR recA1 endA1 hsdR17($r_K^-$, $m_K^+$) phoA supE44λ⁻thi-1 gvrA96 relA1 | Invitrogen Carlsbad, CA |
| P. fluorescens 5R | Naphthalene metabolizing strain, harboring the archetypal NAH plasmid pKA1 | Sanseverino et al., 1993 |

4.3.1 Bioluminescent Bioreporter Cell Line Responsive to AHL Inducer Molecules

Only a single bioluminescent bioreporter cell line needs to be constructed since its function, to respond to AHL molecules, remains the same regardless of the bacteriophage/pathogen system with which it is coupled. The methods described involve techniques utilized for the successful construction of several bioluminescent bioreporter cell lines for chemical sensing (Table 3).

TABLE 3

Whole cell bioluminescent reporters constructed utilizing the MiniTn5NXlux transposon.

| Bioluminescent Reporter | lux fusion | Reference |
|---|---|---|
| Pseudomonas putida TVA8 | chromosomal-based tod-lux fusion for the detection of toluene | Applegate et al., 1998 |
| Ralstonia eutropha JMP134-32 | tfd-lux to detect the herbicide 2,4-dichlorophenoxyacetic acid (2,4-D) | Hay et al., 2000 |
| Pseudomonas putida FeLux-1 | Ferric uptake regulatory (fur) responsive promoter fused to lux to determine the bioavailability of Fe in aqueous systems | Bright et al., 2000 |

The bioluminescent bioreporter strain is constructed using a promoterless luxCDABE gene cassette in a MiniTn5 transposon designated MiniTn5NXlux (Applegate et al., 1998). This construct contains a unique NotI/XbaI cloning site allowing for direct insertion of promoter fragments. The MiniTN5 transposon containing luxR and its associated promoter element (hereafter designated as luxR-luxproluxI) is constructed by amplifying the luxR gene and the divergent promoter and luxI using appropriate primers containing base modification to generate NotI and XbaI restriction sites to allow directional cloning of the luxR-luxproluxI fragment into the transposon's unique NotI/XbaI cloning site (FIG. 3). The fragment is amplified using Touchdown PCR to accommodate the primer modifications and to decrease spurious amplification products (Don et al., 1991).

The MiniTn5/luxR-lux$_{pro}$ transposon is transformed into E. coli SV17-1 (pir) and biparentally mated into Pseudomonas fluorescens 5R. P. fluorescens 5R is highly suitable for this purpose because it generates the highest levels of light of any strain tested (King et al., 1990). Transconjugants are selected on minimal media supplemented with kanamycin (50 mg/L) and salicylate as a sole carbon and energy source. Salicylate metabolism permits isolation of the recombinant Pseudomonas from the E. coli donor strain since it harbors the archetypal NAH plasmid pKA1 which allows the strain to utilize naphthalene and salicylate as carbon and energy sources. Transconjugants are screened for insertions into the plasmid as opposed to the chromosome to provide increased copy number of the genetic reporter genes. The plasmid is highly stable and will also allow mobilization into other strains if necessary.

4.3.2 LuxI Bacteriophage

A wide variety of bacteriophage may be genetically incorporated with the luxI gene to independently detect unique pathogenic species. Examples of pathogens and their associated phage are listed in Table 4. These examples are selected because the listed phage have been extensively utilized for the epidemiological typing of their specific pathogen. Based on phage adsorption constants, latency periods, and lysis times in pure culture studies, temperate phage are likely to yield higher AHL concentrations and subsequent higher light levels upon host infection, while virulent phage will yield faster response times but much lower light levels. This is based on studies by Carriere et al. (1997) using luxAB reporter phage for Mycobacterium tuberculosis, where it was demonstrated that rapid cell lysis by virulent phage resulted in a rapid reduction in light output while temperate reporter phage yielded light responses of longer duration due to accumulation of luciferase protein in the host. L. monocytogenes virulent (A511) and temperate (A118) phage, which have been fully sequenced, are available for use in a homologous recombination method described below to generate luxI integrated phage.

TABLE 4

Bacteriophage and their corresponding pathogenic hosts

| | Host Pathogen | Reference |
|---|---|---|
| Virulent Phage | | |
| KH1 | *Escherichia coli* O157:H7 | Kudva et al., 1999 |
| E79 | *Pseudomonas aeruginosa* | Hayashi, 1981 |
| Felix O-1 | *Salmonella* spp. | Stewart et al., 1998 |
| Twort | *Staphylococcus aureus* | Loessner et al., 1998 |
| φ4 | *Campylobacter* spp. | Frost et al., 1999 |
| A511 | *Listeria monocytogenes* | Loessner et al., 1996 |
| Temperate Phage | | |
| φV10 | *Escherichia coli* O157:H7 | Khakhria et al., 1990 |
| G101 | *Pseudomonas aeruginosa* | Miller et al., 1974 |
| P22 | *Salmonella* spp. | Chen and Griffiths, 1996 |
| φ11 | *Staphylococcus aureus* | Stewart et al., 1985 |
| φC | *Campylobacter* spp. | Bokkenheuser et al., 1979 |
| A118 | *Listeria monocytogenes* | Loessner et al., 2000; van der Mee-Marquet et al., 1997 |

Utilizing standard PCR techniques, primers may be designed to amplify the luxI gene from *V. fischeri*. The 5' primer is designed to contain stop codons in all three reading frames of the luxI start codon and ribosomal binding site to prevent frame shifting resulting in fusion proteins. Ribosomal binding sites are also modified to provide optimal expression in the target organism. The resultant fragments are cloned into the TA cloning vector PCR™ II according to the manufacturer's protocol. Transformants with inserts are subjected to restriction analysis to verify fragment size and orientation.

Strains containing inserts in the proper orientation ($lac_{pro}$luxI) are screened for the production of the diffusible AHL signal by testing the supernatant for induction activities with an AHL-responsive bioluminescent reporter strain. The assay is conducted by growing the *E. coli* cultures containing correct inserts to an optical density of 1.0 at 546 nm followed by centrifugation. The supernatant is tested by adding aliquots to the reporter strain. Those clones producing functional AHL are sequenced for verification.

4.4 Bioluminescent Response

The light response generated by bioluminescent bioreporters, whether of bacterial or bacteriophage nature, is typically measured with optical transducers such as photomultiplier tubes, photodiodes, microchannel plates, or charge-coupled devices. Some means of transferring the bioluminescent signal to the transducer is additionally required, which necessitates the need for fiber optic cables, lenses, or liquid light guides. What typically results is a large, bulky instrument anchored to power and optic cables that proves unsuitable for 'in-the-field' use. The Azur Corporation, (Carlsbad, Calif.), among others, has developed battery-operated, hand-held photomultiplier units that can be directly interfaced with a laptop computer.

"Field-friendly" bioluminescence detectors are made using integrated circuit optical transducers that directly interface with bioreporter microorganisms (Simpson et al., 2001). These bioluminescent bioreporter integrated circuits (BBICs) are contained within an approximate 5 mm$^2$ area and consist of two main components; photodetectors for capturing the on-chip bioluminescent bioreporter signals and signal processors for managing and storing information derived from bioluminescence. If required, remote frequency (RF) transmitters can also be incorporated into the overall integrated circuit design for wireless data relay. Since all required elements are completely self-contained within the BBIC, operational capabilities are realized by simply exposing the BBIC to the desired test sample.

4.5 Use of the Bioluminescent Pathogen Detection System

4.5.1 Bioreporter Cell Line

Detection limits, response times, saturation kinetics and basal expression levels of lux (Winson et al., 1998) are observed in the bioreporter cell lines using standardized bioavailability assays (Heitzer et al., 1992). The bioreporter cells are grown in yeast extract-peptone-glucose (YEPG) medium to exponential phase ($OD_{546}$=0.35) whereupon 100 μl aliquots are transferred to 96-well microtiter plates. Acyl homoserine lactone (AHL) at concentrations ranging from 0.01 to 1000 ppm is added to microtiter wells and light readings are measured continuously in a scintillation counter over a 24 hour period. Background levels of bioluminescence due to basal expression of the lux gene are determined in vials containing no AHL.

Plotting of background-corrected bioluminescence versus time generates standard curves indicating detection limits and response times. Standard HPLC techniques are used for analytical measurement of AHL concentrations (Winson et al., 1998). Once baseline measurements are obtained, tests utilizing the bioreporter strain in conjunction with varying concentrations of luxI bacteriophage and associated pathogen are similarly performed in microtiter plate formats to determine detection limits, response times, saturation kinetics, and background induction.

Measurements may also be taken using an Azur DeltaTox (Carlsbad, Calif.) photomultiplier device. The Azur photomultiplier is a battery-operated, hand-held unit that interfaces directly to a laptop computer, thus making it ideal for 'in-the-field' monitoring. Parameters such as temperature and pH are closely monitored to identify possible effects on bioreporter response. A negative control consisting of samples void of bacteriophage is used to account for intrinsic AHL molecules.

Sample analysis may also be performed using an integrated circuit photodetector, i.e. a test bed of integrated circuits for replicate measurement of induced bioreporter bioluminescence. Such analysis utilizes integrated circuits linked to a flow cell system through which the desired test substance passes. Resulting bioluminescent responses are recorded by the integrated circuit and downloaded to a computer interface.

4.5. 2 Effect of Physiological State of Reporter Bacteria

The physiological state of the bacteria may influence the degree of bioreporter response, because luminescence requires active replication of the bacteriophage and bacteriophage-coded products (i.e. acyl-homoserine lactone synthetase) within the pathogen. Assays using log-phase cells may overestimate the sensitivity of the bioreporter system for field conditions. Thus studies are conducted with strains of interest under a range of physiological states, effected by either starvation or disinfectant treatment with chlorine. Starvation is induced by harvesting log-phase cells, then rinsing (3 times) and storing these cells in minimal salts media. Stored cells are sampled after 0 hr, 1 hr, 1 d, 3 d, and 7 d to provide a wide range of metabolic states (Morita, 1982). Similarly washed log-phase suspensions are dosed with a range of chlorine levels (0,0.5, 1, 2, and 3 mg/L) for 2 minutes to provide a gradient in the number of active cells (Boulos et al., 1999).

Samples from the various starvation times and chlorine doses are assessed for bioreporter response and several types of cell counts are performed including 1) total direct counts using acridine orange (AO) staining (Hobbie et al. 1977), 2) viable cells using the LIVE/DEAD test kit (Molecular Probes, Eugene, Oreg.), and 3) respiring cells using 5-cyano-2,3-ditotyl tetrazoloium (CTC). Bioreporter tests may utilize an Azur Deltatox photomultiplier unit following standard procedures defined during baseline studies. Of the various cell counts, AO counts provide an estimate of total cells present, which should remain relatively constant irrespective of starvation time or chlorine treatment level. CTC counts provide an estimate of actively respiring cells as a result of reduction of the colorless CTC dye to fluorescent formazan in cells with active electron transport activity. CTC response (both in terms of the number of respiring cells and the fluorescence per cell) rapidly responds to carbon source availability (Cook and Garland, 1997) and stress such as chlorine treatment (Boulos et al., 1999).

Two nucleic acid-binding stains in the LIVE/DEAD Baclight kit differentiate total and viable cells. The first, SYTO 9, passes into all cells and results in a fluorescent green stain. The second, propidium iodide, is able to penetrate only those cells with damaged membranes, staining them red. The dual staining results in separate estimates of live (green) and dead (red) cells using membrane integrity as the distinguishing characteristic. Viable counts estimated from LIVE/DEAD assays have been shown to be less responsive to stress than CTC counts (Boulos et al., 1999; Braux et al., 1997). Concurrent analysis of samples with these different techniques allows a direct estimation of the role that respiration and viability have on the bioreporter response. It is important to understand the degree to which viable, but not actively respiring, cells respond in the biosensor assay. If the response of viable but non-respiring cells is weak, then potentially virulent cells may go undetected.

4.5.3 Effect of Sample Matrix on Bioluminescence

Sample matrix (i.e., particulate matter including microorganisms generated from rinsing or blending the sample material with the bioreporter) may affect the bioreporter response. Particulate matter may bind cells and block infection of the bacteriophage, resulting in non-specific phage binding, and/or cause general quenching of the light signal. This could reduce the detection limit of the bioreporter. On the other hand, non-specific infection, although unlikely, could result in false positive responses.

In some embodiments of the invention, it may be desirable to immobilize the bioreporter cells in a stabilizing matrix. Alginate has been successfully used for encapsulation of cells without adverse effects on viability. Long-term viability (weeks to months) is possible as long as the alginate-encased cells remain moist. Latex copolymers have also been reported to be useful for immobilizing *E. Coli* and maintaining viability (Lyngberg et al., 1999). Other matrices include carrageenan, acrylic vinyl acetate copolymer, polyvinyl chloride polymer, sol-gel, agar, agarose, micromachined nanoporous membranes, polydimethylsiloxane (PDMS), polyacrylamide, polyurethane/polycarbomyl sulfonate, or polyvinyl alcohol. Electrophoretic deposition may also be employed.

4.5.4 Effect of Bioreporter Lyophilization and Assessment of Shelf-Life

A significant advantage in using microorganisms as bioreporters is their ability to undergo lyophilization (freeze-drying), allowing for extended storage from months to years with little loss in viability. It is desirable that the bacteriophage/bioreporter system be placed in a physiological state amenable to long-term storage such that the end-user can simply revive a pellet of cells whenever measurements are required. To assess the shelf-life of bacteriophage and bioluminescent bioreporters of the invention, these two components are lyophilized, resuscitated and induced at various intervals and bioluminescence is measured as described above, in order to provide an overall assessment of long-term bioreporter stability.

5.0 EXAMPLES

5.1 Example 1

Amplification of Bioluminescent Signal in Bioreporter Cells

The detection scheme for quantifying pathogenic targets relies on the ability of AHL molecules to induce bioluminescence in such a manner that it can be correlated with the original number of AHL-producing targets present in the sample. The technique uses the same premise as quantitative PCR with the exception that initial AHL concentrations, as opposed to nucleic acid concentrations, allow for differential detection of the exponential increase in signal, i.e. bioluminescence, in the reporter cells (Heid et al., 1996).

Amplification of the bioluminescent response of the bioreporter cells occurs through the autoinduction mechanism of *V. fischeri*. AHL is released into the extracellular environment following target cell infection by the biosensor, i.e a luxI-bacteriophage. Uptake of AHL by neighboring bioluminescent bioreporter cells induces light production in the latter cells, as well as production of more AHL. This AHL in turn stimulates more production of light. The result is a cascade effect that ultimately generates intense bioluminescent light due to involvement of multiple binding episodes in multiple bioluminescent cells.

FIG. 4 shows the results of an experiment in which *V fischeri* were used as bioreporter cells to show the effect of varying concentrations of exogenously added inducer on the time required for induction of a measurable bioluminescent response. An overnight culture of *V. fischeri* was diluted to an $OD_{546}$ of 0.01. Standard dilutions of N-(3-oxohexanoyl) homoserine lactone (Quorum Sciences) were prepared by resuspending 213.2 mg in 1 mL of acidified ethyl acetate resulting in a 100 mM stock followed by dilutions in acidified ethyl acetate. Assays were performed by placing 100 µl of N-(3-oxohexanoyl) homoserine lactone/ethyl acetate solution into shell vials followed by evaporation. One mL aliquots of V. fischeri (prepared as above) were added to the test vials. Vials were then shaken at 140 rpm and light measurements were taken at time zero and at 30-minute intervals using a Zylux portable luminometer. Data were plotted as photons per second versus time and were the average of three replicates.

In the data analysis, a threshold line is used to discriminate between samples (FIG. 4). The line provides a value in photons per second at which the bioluminescent bioreporter is autoinduced. This value is determined by the characteristics of the curve on the graph. The onset of autoinduction is indicated by the rapid increase in the slope of the curve. The autoinduction of the control sample is used to set the threshold line of the assay. Once the value of the threshold line is determined, the sample data are analyzed according to the time at which autoinduction occurs. The higher the concentration of the inducer, the sooner the onset of autoinduction. This can be used in a qualitative or quantitative format depending on the application.

The results show that the higher the initial concentration of homoserine lactone, the sooner the onset of light production is detected (FIG. 4) All samples eventually achieved similar light levels, however it is the initiation of the geometric increase in light that allows for quantification of inducer-producing targets. The results demonstrate that homoserine lactone molecules amplify the lux-based bioluminescent signal in a quantifiable fashion.

In the bacteriophage/bioreporter system, the target bacterium is infected by a specific bacteriophage carrying the luxI gene. After infection, the bacterium gains the ability to produce the inducer, acyl homoserine lactone (AHL) protein. The more phage infection events that occur, the higher the concentration of AHL, and the shorter the time required for light production in the bioluminescent bioreporter cells. The time decrease between the control and the samples is used to measure the number or amount of bacteria infected by the luxI-bacteriophage.

5.2 Example 2

Exemplary Strains of LuxI Bacteriophage

Because the genomes of L. monocytogenes phage A511 and A118 have been characterized, luxI integration in these bacteriophage is therefore accomplished through homologous recombination. The basic strategy follows that of the A511::luxAB phage described by Loessner et al., (1996). The luxI construct developed as described in section 4.3.2, with appropriate ribosome binding sites for L. monocytogenes, is amplified with a set of primers containing flanking DNA sequences at the 3' end of the cps gene in phage A511 and A118. The product is amplified and subsequently inserted into the phage by recombination, and bacteriophage are screened and enriched essentially as described by Loessner et al., (1996). Since the production of AHL is the phenotype of choice, supernatants of primary lysates are examined for their ability to induce the lux genes in the reporter strain. The selected phage containing luxI is verified using RFLP analysis.

For uncharacterized phage genomes, the transposon mutagenesis method of Waddel and Poppe, 1999 is used for generating luxI phage constructs. The phage are mutagenized using a promoterless luxI gene in a MiniTn5 transposon. The MiniTn5luxI transposon is constructed by inserting the appropriate previously constructed luxI into the unique cloning site of pUTK214 (Applegate et al., 1998). The construct is transformed into E. coli SV17-1(pir). Transformants are screened for inserts using restriction fragment analysis. Once the appropriate MiniTn5luxI transposons are obtained they are used to mutagenize (via biparental mating) the appropriate phage for the specific application. Phage are screened as previously described (Waddell and Poppe, 1999), except kanamycin is used for selection. Phage showing the Km$^R$ phenotype are further screened for the production of acyl homoserine lactone (AHL) using the bioluminescent reporter strain as described above. Phage that exhibit significant AHL production are utilized in the detection assays.

The M13 bacteriophage is a useful model in illustrating a system capable of detecting various pathogens. Additonally, luxI genes may be appropriately modified to be expressed in the following organisms: E. coli O157:H7, L. monocytogenes, Salmonella spp., Campylobacter spp., B. anthracis, B. thuringiensis and B. subtilus.

5.3 Example 3

Detection of Bacterial Pathogens in Food

Four pathogens of particular concern to the food industry include Salmonella, Listeria monocytogenes, Escherichia coli O157:H7, and Campylobacter. Based on recent estimates, these four bacterial types cause two-thirds of all food-related deaths in the U.S., and more than 95% of food-related deaths caused by bacteria (Mead et al., 1999). Salmonella-related illness has been linked to cantaloupe (Riess et al., 1990), alfalfa sprouts (Mahon et al., 1997), tomatoes (Hedberg et al., 1994) and watermelon (del Rosario et al., 1995). Salmonella has also been isolated from a wide variety of fresh vegetables, including artichoke, cabbage, cauliflower, celery, eggplant, endive, fennel, lettuce mustard cress, parsley, and spinach (Sumner and Peters, 1997).

Listeria monocytogenes causes serious human disease manifested by sepsis and meningitis. It is commonly found on vegetables (Beuchat, 1996), including lettuce (Beuchat and Brackett, 1990), tomatoes (Beuchat and Brackett, 1991), asparagus, broccoli, and cauliflower (Berrang et al., 1989). A documented listeriosis outbreak has been associated with cabbage (Schlech et al., 1983). Growth of L. monocytogenes can occur at cool (5–15° C.) storage temperatures (Berrang et al., 1989).

E. coli O157:H7 is an emerging human pathogen first linked to food illness (i.e., fast food hamburgers) outbreaks in 1982. It produces enterohemorrhagic toxins that can lead to death, particularly in the very young and old. Cattle appear to be a primary reservoir, but E. coli O157:H7 has been linked to outbreaks from cantaloupe, broccoli, and potentially lettuce (Sumner and Peters, 1997). The organism can survive and grow on cubed melon and watermelon (del Rosario and Beuchat, 1995), and has been isolated from cabbage, celery, cilantro, and coriander.

Campylobacter is an emerging pathogen that causes acute gastroenteritis and has been identified as a common antecedent to Guillan-Barre syndrome, an acute neurological disease. Illness is most commonly associated with consumption of contaminated poultry and raw milk, although Campylobacter has been linked to raw fruits and vegetables (Bean and Griffin, 1990; Harris et al., 1986).

The invention may be used for detection of pathogens important for food safety, with appropriate consideration for the nature of the sample under analysis. For example, the bioreporter response may be affected by sample matrix, i.e particulate material generated from rinsing or blending vegetable matter. Particulate material may bind target cells and block infection by the bacteriophage and/or it may cause general quenching of the light signal emitted from the bioreporter cells. Samples obtained from lettuce and tomato may be analyzed to test the effects of sample matrix on the bioreporter assay. Lettuce and tomato are presented as examples because both plant types are commonly consumed fresh produce that have been reportedly contaminated with some, if not all, of the pathogens identified as significant to the food industry. Additionally, the two crops represent distinctive types of plant material (i.e., leafy vegetables versus pulpy fruit) with potentially distinctive matrix characteristics.

Surface washings of lettuce are produced by shaking aseptically cut strips in sterile Tris buffer for 2 hr, and homogenized samples are obtained using a stomacher blender (Donegan et al., 1991; Jacques and Morris, 1995). Tomatoes are surface rinsed by gently hand rubbing tomatoes placed in sterile bags containing sterile buffer and homogenized using a stomacher blender (Zhuang et al., 1995). Other assays use blended samples of lettuce and tomato. Log-phase cells are introduced at levels well within the detection limits defined by the baseline studies and results with added vegetable matter are compared with controls.

Other tests are designed to provide baseline information on the effectiveness of the biosensor to detect contamination in plant production, processing, and distribution systems. Specific amounts of the pathogens are added to plant material either during the plant growth cycle or immediately after harvest. Survival of the pathogen is compared by monitoring its survival until harvest or after storage using the biosensor and comparing with results obtained by reverse transcriptase- quantitative PCR (Heid et al., 1996), as described below.

Tomato and lettuce are used as examples of use of the invention to detect pathogens during food production. The production cycle for lettuce (cv Waldmann's Green) is typically 28 days in the controlled environmental chambers (Wheeler et al., 1994). Pathogens are added to leaves at day 7, and subsequently sampled after 1, 7, 14, and 21 d. The production cycle for tomato (cv. Reimann Phillip) in controlled environmental chambers is 90 days, although ripe fruit are harvested beginning at day 60 (Mackowiak et al., 1999). Immature fruit present on day 60 are inoculated with pathogens, and these fruit are removed from the plants after 1, 7, 14, and 21 d. or other suitable intervals.

Inoculation of plant material is accomplished by pipetting small volumes (~5 µl) at multiple spots on the leaf or fruit to minimize aerosol formation and associated safety issues associated with spraying the pathogens on the plants. The level of inoculation depends on detection limits established in baseline studies. Post-harvest inoculation is performed by submerging lettuce leaves or tomato fruit in bacterial suspensions with gentle agitation for 2 min followed by air drying under a laminar flow hood (Zhuang et al., 1995). Material is stored in incubators controlled at either 5° or 25° C. to simulate storage at refrigeration or room temperature conditions, respectively, and sampled after 1, 2, 4, 8, and 16 days.

Reverse transcriptase quantitative PCR (RTQ-PCR) is a method used to quantify either DNA or RNA copy number in a sample of extracted nucleic acids (Heid et al., 1996). The method is based on the targeted amplification of either DNA (by means of PCR) or RNA (by means of Reverse Transcriptase-PCR) and the real-time kinetic detection of PCR product as it accumulates at each cycle in the ABI 7700 Sequence Detection System (Foster City, Calif.). Detection of the specific target molecule is accomplished in a single PCR reaction with primers flanking the area of interest and a diagnostic probe dual labeled with a fluorescent reporter dye and a quencher. Perfectly annealed probes are cleaved by the 5'-nuclease activity of Taq™ polymerase (Hoffman-La Roche, Mannheim, Germany), resulting in an increase of reporter signal. The fluorescent signal generated by labeled PCR products is quantified in real time by means of laser-induced fluorometry and charge coupled devices (CCD) detection. The method and instrumentation are compatible with multiple reporter chemistries.

The TaqMan™ assay (Applied Biosystems, Foster City, Calif.) is capable of accurately detecting 5 copies of target in a background of 500 ng of non-target DNA or RNA (e.g., 5 organisms per sample) and is accurate over a five order of magnitude dynamic range (i.e., 5 to $10^6$ copies). RTQ-PCR is at present the most sensitive method available to detect and quantify molecular targets for pathogen detection. As such, it represents the best approach for evaluating biosensor sensitivity.

The specificity of primer-directed PCR amplification in combination with probe hybridization is superior to membrane-bound nucleic acid hybridization and allows the quantitative detection of either DNA or RNA. The use of RT-PCR to detect and quantify mRNA and rRNA affords the opportunity to determine the relative ratios of actively respiring versus non-viable bacteria and therefore identify the potential for pathogen outgrowth from processed food and agricultural commodities. Both rRNA and mRNA content are correlated with the physiological state of the cell or community; rRNA content generally increasing with growth rate.

Salmonella detection for QPCR is accomplished using two primer-probe detection systems that target different molecular markers specific for Salmonella. The TaqMan™ Salmonella PCR Amplification and Detection Kit (Applied Biosystems, Foster City, Calif.) is based on a 287 bp invA gene product and has been demonstrated for use in the detection of Salmonella spp. in raw meat products (Chen et al., 1997; Kimura et al., 1999). The second primer set amplifies either a 173 bp or 107 bp product from a *Salmonella typhimurium* specific region of the phase 1 flagellin filament gene (Marsh et a., 1998). Its use has been described in the quantitative detection of viable but non-culturable *S. typhimurium* populations in soil systems.

*Listeria monocytogenes* detection for QPCR targets the hemolysin A (hlyA) transcript that is unique to Listeria. The hlyA detection system, developed by Norton and Batt, (1999), allows the quantitative detection of viable Listeria populations over three orders of magnitude using a 210-bp segment of the transcribed hlyA gene as target.

*Escherichia coli* O157:H7 detection for QPCR utilizes the 5' nuclease assay developed by Oberst et al. (Oberst et al., 1998) which targets the intimin protein encoded by eaeA. The eaeA assay generates a 631 bp segment of the gene which contains target sequence that may be specifically detected by one of four possible probe sequences.

*Campylobacter jejuni* detection utilizes the nested PCR approach of Winters et al. (1998; 2000) in a modified 5' nuclease assay. The initial PCR amplification generates a 159 bp product which is then used as template for a second PCR amplification using the original forward primer and a new reverse primer complementary to a region internal to the 3' end of the first amplification product. The nested product yields a 122 bp *C. jejuni* product but no product from *C. coli*.

5.4 Example 4

Bioluminescent/Bioreporter Device in Compact Disk Format

FIG. 5 depicts an embodiment of the invention configured in a compact disk (CD) format similar to the LabCD centrifugal microfluidic systems described by Madou et al.(2001). The bacteriophage/bioluminescent bioreporter system is contained in the outer wells. Each of the four outer wells contains luxI-containing bacteriophage specific for a unique bacterial pathogen, as well as bioluminescent bioreporter cells engineered to respond to the luxI acyl-homoserine lactone (AHL) auto-inducer. In some embodiments, the bacteriophage and bioreporter cells are in an encapsulation matrix.

The homogenized sample or washings from the sample is channeled into the center well and the CD is spun to distribute the sample to each well. If pathogens are present in the sample, infection by the bacteriophage occurs and subsequent bioluminescent signals are generated. Each well is centered over an integrated circuit optical transducer, allowing for bioluminescence to be measured, an assessment of pathogen incidence and concentration to be made, and corresponding data to be downloaded to a digital screen. Testing of another sample simply requires insertion of a new CD. Wells containing only bioluminescent bioreporter cells serve as background controls.

6.0 REFERENCES

Applegate, B., C. Kelley, L. Lackey, J. McPherson, S. Kehrmeyer, F.-M. Menn, P. Bienkowski, and G. Sayler. 1997. Pseudomonas putida B2: a tod-lux bioluminescent reporter for toluene and trichloroethylene co-metabolism. J. Ind. Microbiol. Biotech. 18:4–9.

Applegate, B. M., S. R. Kehrmeyer, and G. S. Sayler. 1998. A chromosomally based tod-luxCDABE whole-cell reporter for benzene, toluene, ethylbenzene, and xylene (BTEX) sensing. Appl. Environ. Microbiol. 64:2730–2735.

Bean, N. H., and P. M. Griffin. 1990. Foodbome outbreaks in the United States, 1973–1987: pathogens, vehicles, and trends. J. Food Protect. 53:807–814.

Berrang, M. E., R. E. Brkett, and L. R. Beuchat. 1989. Growth of Listeria onocytogenes on fresh vegetables stored under controlled atmosphere. J. Food Protect. 52:702–705.

Beuchat, L. R. 1996. Listeria monocytogenes: incidence on vegetables. Food Control 7:223–228.

Beuchat, L. R., and R. E. Brackett. 1990. Growth of Listeria monocytogenes on lettuce as influenced by shredding, chlorine treatment, modified atmosphere, packaging, temperature, and time. J. Food Sci. 55:575–578.

Beuchat, L. R., and R. *E. Brackett*. 1991. Growth of Listeria monocytogenes on tomatoes as influenced by shredding, chlorine treatment, modified atmosphere, packaging, temperature, and time. Appl. Environ. Microbiol. 57:1367–1371.

Blostein, J. 1991. An outbreak of Salmonella javiana associated with consumption of watermelon. J. Environ. Health 56:29–31.

Bokkenheuser, V. D., N. J. Richardson, J. H. Bryner, D. J. Roux, A. B. Schutte, H. J. Koornhof, I. Freiman, and E. Hartman. 1979. Detection of enteric campylobacteriosis in children. J. Clin. Microbiol. 9:227–232.

Boulos, L., M. Prevost, B. Barbeau, J. Collier, and R. Desjardins. 1999. LIVE/DEAD Baclight: application of a new rapid staining method for direct enumeration of viable and total bacteria in drinking water. J. Microbiol. Methods 37:77–86.

Braux, A. S., J. Minet, Z. Tamanai, G. Riou, and M. Cormier. 1997. Direct enumeration of injured Escherichia coli cells harvested onto membrane filters. J. Microbiol. Methods 31:1–8.

Bright, N. G., B. Applegate, M. L. Eldridge, G. S. Sayler, and S. W. Wilhelm. 2000. Development of a bioluminescent reporter for the determination of aqueous iron bioavailability. Presented at the American Society for Microbiology Annual Meeting, Los Angeles, Calif.

Carriere, C., P. F. Riska, O. Zimhony, J. Kriakov, S. Bardarov, J. Bums, J. Chan, and W. R. Jacobs. 1997. Conditionally replicating luciferase reporter phages: improved sensitivity for rapid detection and assessment of drug susceptibility of *Mycobacterium tuberculosis*. Journal of Clinical Microbiology 35:3232–3239.

Chen, J., and M. W. Griffiths. 1996. Salmonella detection in eggs using lux+bacteriophages. J. Food Protection 59:908–914.

Chen, S., A. Yee, M. W. Griffiths, C. Larkin, C. T. Yamashiro, R. Behari, C. Paszko-Kolva, K. Rahn, and S. A. de Grandis. 1997. The evaluation of a fluorogenic polymerase chain reaction assay for the detection of Salmonella species in food commodities. J. Food Microbiol. 35:239–250.

Cook, K. L., and J. L. Garland. 1997. The relationship between electron transport activity as measured by CTC reduction and $CO_2$ production in mixed microbial communities. Microbiol. Ecol. 34:237–247.

de Lorenzo, V., S. Fernandez, M. Herrero, U. Jakubzik, and K. N. Timmis. 1993. Engineering of alkyl- and haloaromatic-responsive gene expression with mini-transposons containing regulated promoters of biodegradative pathways of Pseudomonas. Gene 130:41–46.

de Lorenzo, V., M. Herrero, U. Jakubzik, and K. N. Timmis. 1990. Mini-Tn5 transposon derivatives for insertion mutagenesis, promoter probing, and chromosomal insertion of cloned DNA in gram-negative eubacteria. J. Bacteriol. 172:6568–6572.

del Rosario, B. A., and L. R. Beuchat. 1995. Survival and growth of enterohemorrhagic Escherichia coli O157:H7 in cantaloupe and watermelons. J. Food Protect. 58:105–107.

Don, R. H., P. T. Cox, B. J. Wainwright, K. Baker, and J. S. Mattick. 1991. 'Touchdown' PCR to circumvent spurious priming during gene amplification. Nuc. Acids Res. 19:4008.

Donegan, K. K., C. Maytac, R. Seidler, and L. A. Porteous. 1991. Evaluation of methods for sampling, recovery, and enumeration of bacteria to the phylloplane. Appl. Environ. Microbiol. 57:51–56.

Engebrecht, J., K. Nealson, and M. Silverman. 1983. Bacterial bioluminescence: isolation and genetic analysis of functions from Vibrio fischeri. Cell 32:773–781.

Frost, J. A., J. M. Kramer, and S. A. Gillanders. 1999. Phage typing of Campylobacter jejuni and Campylobacter coli and its use as an adjunct to serotyping. Epidemiol. Infect. 123:47–55.

Harris, M. V., T. Kimball, N. S. Weiss, and C. Nolan. 1986. Dairy products, produce, and other non-meat foods as possible sources of Campylobacter jejuni and Campylobacter enteritis. J. Food Protect. 29:347–351.

Hay, A. G., B. M. Applegate, N. G. Bright, and G. S. Sayler. 2000. A bioluminescent whole-cell reporter for detection of 2,4-dichlorophenoxyacetic acid and 2,4-dichlorophenol in soil. Applied and Environmental Microbiology 66:4589–4594.

Hayashi, T. 1981. Fundamental studies on the bacteriophages for typing *Pseudomonas aeruginosa* and their propagating strains. Tropical Medicine 23:119–134.

Hedberg, C. W., K. L. MacDonald, and M. T. Osterholm. 1994. Changing epidemiology of foodborne disease: a Minnesota perspective. Clinical Infectious Diseases 18:671–682.

Heid, C. A., J. Stevens, K. J. Livak, and P. M. Williams. 1996. Real time quantitative PCR. Genome Res. 6:986–994.

Heitzer, A., K. Malachowsky, J. E. Thonnard, P. R. Bienkowski, D. C. White, and G. S. Sayler. 1994. Optical biosensor for environmental on-line monitoring of naphthalene and salicylate bioavailability with an immobilized bioluminescent catabolic reporter bacterium. Appl. Environ. Microbiol. 60:1487–1494.

Heitzer, A., O. F. Webb, J. E. Thonnard, and G. S. Sayler. 1992. Specific and quantitative assessment of naphthalene and salicylate bioavailability by using a bioluminescent catabolic reporter bacterium. Appl. Environ. Microbiol. 58:1839–1846.

Hellingwerf, K. J., W. C. Crielaard, M. J. T. de Mattos, W. D. Hoff, R. Kort, D. T. Verhamme, and C. Avignone-Rossa. 1998. Current topics in signal transduction in bacteria. Antonie van Leeuwenhoek 74:211–227.

Hobbie, J. E., R. J. Daley, and S. Jasper. 1977. Use of nucleopore filters for counting bacteria by fluorescence microscopy. Appl. Environ. Microbiol. 33:1225–1228.

Jacques, M., and C. E. Morris. 1995. A review of issues related to the quantification of bacteria from the phylloplane. FEMS Microbiol. Ecol. 18:1–14.

Khakhria, R., D. Duck, and H. Lior. 1990. Extended phage-typing scheme for Escherichia coli O157:H7. Epidemiol. Infect. 105:511–520.

Kimura, B., S. Kawasaki, T. Fuji, J. Kusunoki, T. Itoh, and S. J. Flood. 1999. Evaluation of TaqMan PCR assay for detecting Salmonella in raw meat and shrimp. J. Food Protect. 62:329–335.

King, J. M. H., P. M. DiGrazia, B. Applegate, R. Burlage, J. Sanseverino, P. Dunbar, F. Larimer, and G. S. Sayler. 1990. Rapid, sensitive bioluminescence reporter technology for naphthalene exposure and biodegradation. Science 249:778–781.

Kodikara, C. P., H. H. Crew, and G. S. A. B. Stewart. 1991. Near on-line detection of enteric bacteria using lux recombinant bacteriophage. FEMS Microbiol. Lett. 83:261–266.

Kudva, I. T., S. Jelacic, P. I. Tarr, P. Youderian, and C. J. Hovde. 1999. Biocontrol of Escherichia coli O157 with O157-specific bacteriophages. Appl. Environ. Microbiol. 65:3767–3773.

Layton, A. C., M. Muccini, M. M. Ghosh, and G. S. Sayler. 1998. Construction of a bioluminescent reporter strain to detect polychlorinated biphenyls. Appl. Environ. Microbiol. 64:5023–5026.

Loessner, M. J., S. Gaeng, G. Wendlinger, S. K. Maier, and S. Scherer. 1998. The two-component lysis system of Staphylococcus aureus bacteriophage Twort: a large TTG-start holin and an associated amidase endolysin. FEMs Microbiology Letters 162:265–274.

Loessner, M. J., R. B. Iman, P. Lauer, and R. Calendar. 2000. Complete nucleotide sequence, molecular analysis and genome structure of bacteriophage A118 of Listeria monocytogenes: implications for phage evolution. Mol. Microbiol. 35:324–340.

Loessner, M. J., C. E. D. Rees, G. S. A. B. Stewart, and S. Scherer. 1996. Construction of luciferase reporter bacteriophage A511::luxAB for rapid and sensitive detection of viable Listeria cells. Appl. Environ. Microbiol. 62:1133–1140.

Lyngberg, O. K., D. J. Stemke, J. L. Schottel, and M. C. Flickinger. 1999. A single-use luciferase-based mercury biosensor using *Escherichia coli* HB101 immobilized in a latex copolymer film. Journal of Industrial Microbiology & Biotechnology 23(1):668–676.

Mackowiak, C. L., G. W. Stutte, R. M. Wheeler, L. M. Ruffe, and N. C. Yorio. 1999. Tomato and soybean production on a shared recirculating hydroponic system. Acta Horticulturae 481:259–266.

Madou, M. J., Y. Lu, S. Lai, C. G. Koh, L. J. Lee, and B. R. Wenner. 2001. A novel design on a CD disc for 2-point calibration measurement. Sensors Actuators A 91:301–306.

Mahon, B. E., A. Ponka, W. Hall, K. Komatsu, L. R. Beuchat, S. Dietrich, A. Siitonenm, G. Cage, M. Lambert-Fair, P. Hayes, N. H. Bean, P. M. Griffin, and L. S. Slutker. 1997. An international outbreak of Salmonella infection caused by alfalfa sprouts grown from contaminated seeds. J. Infect. Dis. 175:876–882.

Marks, T., and R. Sharp. 2000. Bacteriophages and biotechnology: a review. J. Chem. Technol. Biotechnol. 75:6–17.

Marsh, P., N. Z. Morris, and E. M. H. Wellington. 1998. Quantitative molecular detection of Salmonella typhimurium in soil and demonstration of persistence of an active but non-culturable population. FEMS Microbiol. Ecol. 27:351–363.

Mead, P. S., L. S. Slutker, V. Dietz, L. F. McCaig, J. S. Bresee, C. Shapiro, P. M. Griffin, and R. V. Tauxe. 1999. Food-related illness and death in the United States. Emerging Infectious Diseases 5:607–625.

Meighen, E. A. 1991. Molecular biology of bacterial bioluminescence. Microbiol. Rev. 55:123–142.

Miller, R. V., J. M. Pemberton, and K. E. Richards. 1974. F116, D3, and G101: temperate bacteriophages of *Pseudomonas aeruginosa*. Virology 59:566–569.

Morita, R. Y. 1982. Starvation-survival of heterotrophs in the marine environment. Adv. Microb. Ecol. 6:171–198.

Norton, D. M., and C. A. Batt. 1999. Detection of viable Listeria monocytogenes with a 5' nuclease PCR assay. Appl. Environ. Microbiol. 65:2122–2127.

Oberst, R. D., M. P. Hays, L. K. Bohra, R. K. Phebus, C. T. Yamashiro, C. Paszko-Kolva, S. J. Flood, J. M. Sargeant, and J. R. Gillespie. 1998. PCR-based DNA amplification and presumptive detection of *Escherichia coli* O157:H7 with an internal fluorogenic probe and the 5' nuclease (TaqMan) assay. Appl. Environ. Microbiol. 64:3389–3396.

Pagotto, F., L. Brovko, and M. W. Griffiths. 1996. Phage-mediated detection of *Staphylococcus aureus* and

*Escherichia coli* using bioluminescence. Bacteriological Quality of Raw Milk 9601:152–156.

Riess, A. A., S. Zaza, C. Langkop, R. V. Tauxe, and P. A. Balke. 1990. A multistate outbreak of *Salmonella chester* linked to imported cantaloupe. Presented at the Interscience Conference on Antimicrobial Agents and Chemotherapy, Washington, D.C.

Ripp, S., B. Applegate, N. G. Bright, R. Stapleton, and G. S. Sayler. 1999a. On-site field analysis of groundwater contaminants utilizing bioluminescent bioreporter microorganisms, American Society for Microbiology Annual Meeting, Chicago, Ill.

Ripp, S., B. Applegate, N. G. Bright, and G. S. Sayler. 2000a. Whole-cell bioluminescent bioreporters for the detection of biogenic amines in food. Presented at the American Society for Microbiology Annual Meeting, Los Angeles, Calif.

Ripp, S., D. E. Nivens, Y. Ahn, C. Werner, J. Jarrel, J. P. Easter, C. D. Cox, R. S. Burlage, and G. S. Sayler. 2000b. Controlled field release of a bioluminescent genetically engineered microorganism for bioremediation process monitoring and control. Environ. Sci. Technol. 34(5):846–853.

Ripp, S., B. M. Applegate, D. E. Nivens, M. J. Paulus, G. E. Jellison, M. L. Simpson, and G. S. Sayler. 1999b. Whole-cell environmental monitoring devices: bioluminescent bioreporter integrated circuits (BBICs). In A. Mulchandani and O. A. Sadik (ed.), Recent Advances in Environmental Chemical Sensors and Biosensors, vol. In press. ACS Press, Clarendon Hills, Ill.

Sanseverino, J., B. Applegate, H. King, and G. Sayler. 1993. Plasmid-mediated mineralization of naphthalene, phenanthrene, and anthracene. Appl. Environ. Microbiol. 59:1931–1937.

Sayler, G. S., U. Matrubutham, F. M. Menn, W. H. Johnston, and R. D. Stapleton. 1998. Molecular probes and biosensors in bioremediation and site assessment, p. 385–434. In S. K. Sikdar and R. L. Irvine (ed.), Bioremediation: Principles and Practice, vol. 1. Technomic Publishing Company, Inc., Lancaster, Pa.

Schlech, W. F., P. M. Lavigne, R. A. Bostoulussi, A. C. Allen, E. V. Haldane, A. J. Wort, A. W. Hightower, S. E. Johnson, S. H. King, E. S. Nicholls, and C. V. Broome. 1983. Epidemic listeriosis—evidence for transmission by food. New Eng. J. Med. 208:203–206.

Simpson, M. L., G. S. Sayler, G. Patterson, D. E. Nivens, E. Bolton, J. Rochelle, C. Arnott, B. Applegate, S. Ripp, and M. A. Guillom. 2001. An integrated CMOS microluminometer for low-level luminescence sensing in the bioluminescent bioreporter integrated circuit. Sensors Actuators B 72:135–141.

Simpson, M. L., G. S. Sayler, S. Ripp, D. E. Nivens, B. M. Applegate, M. J. Paulus, and G. E. Jellison. 1998. Bioluminescent bioreporter integrated circuits form novel whole-cell biosensors. Trends Biotech. 16:332–338.

Steinbrugge, E. G., R. B. Maxcy, and M. B. Liewan. 1988. Fate of Listeria monocytogenes in ready to serve lettuce. J. Food Protect. 51:596–599.

Stewart, G., T. Smith, and S. Denyer. 1989. Genetic engineering for bioluminescent bacteria. Food Sci. Technol. 3:19–22.

Stewart, G. S. A. B., S. A. A. Jassim, S. P. Denyer, P. Newby, K. Linley, and V. K. Dhir. 1998. The specific and sensitive detection of bacterial pathogens with 4 h using bacteriophage amplification. J. Appl. Microbiol. 84:777–783.

Stewart, P. R., H. G. Waldron, J. S. Lee, and P. R. Matthews. 1985. Molecular relationships among serogroup B bacteriophages of *Staphylococcus aureus*. Journal of Virology 55:111–116.

Sumner, S. S., and D. L. Peters. 1997. Microbiology of vegetables, p. 87–114. In D. S. Smith, J. N. Cash, W. K. Nip, and Y. H. Hui (ed.), Processing Vegetables Science and Technology. Technomic Publishing Co., Lancaster, Pa.

Tauxe, R. V. 1992. Epidemiology of Campylobacter jejuni infections in the United States and other industrialized countries, p. 9–19. In I. Nachamkin, M. J. Blaser, and L. Tompkins (ed.), Campylobacterjejuni: Current Status and Future Trends. American Society for Microbiology, Washington D.C.

Ulitzur, S., and J. Kuhn. 1987. Introduction of lux genes into bacteria, a new approach for specific determination of bacteria and their antibiotic susceptibility, p. 463–472. In J. Scholmerich, R. Andreesen, A. Kapp, M. Ernst, and W. G. Woods (ed.), Bioluminescence and Chemiluminescence: New Perspectives. John Wiley & Sons, New York.

van der Mee-Marquet, N., M. J. Loessner, and A. Audurier. 1997. Evaluation of seven experimental phages for inclusion in the international phage set for the epidemiological typing of Listeria monocytogenes. Appl. Environ. Microbiol. 63:3374–3377.

Vanne, L., M. Karwoski, S. Karppinen, and A. M. Sjoberg. 1996. HACCP-based food quality control and rapid detection methods for microorganisms. Food Control 7:263–276.

Waddell, T. E., and C. Poppe. 1999. Construction of mini-Tn10luxABcam/Ptac-ATS and its use for developing a bacteriophage that transduces bioluminescence to Escherichia coli O157:H7. FEMS Microbiol. Ecol. 182:285–289.

Wheeler, R. M., C. L. Mackowiak, J. C. Sager, N. C. Yorio, and W. M. Knott. 1994. Growth and gas exchange of lettuce stands in a closed, controlled environment. J. American Soc. Hort. Sci. 119:610–615.

Winson, M. K., S. Swift, L. Fish, J. P. Throup, F. Jorgensen, S. R. Chhabra, B. W. Bycroft, P. Williams, and G. S. A. B. Stewart. 1998. Construction and analysis of luxCDABE-based plasmid sensors for investigating N-acyl homoserine lactone-mediated quorum sensing. FEMS Microbiol. Lett. 163:185–192.

Winters, D. K., A. E. O'Leary, and M. F. Slavik. 1998. Polymerase chain reaction for rapid detection of Campylobacter jejuni in artificially contaminated foods. Lett. Appl. Microbiol. 27:163–167.

Winters, D. K., and M. F. Slavik. 2000. Multiplex PCR detection of Campylobacter jejuni and Arcobacter butzleri in food products. Mol. Cell Probes 14:95–99.

Wood, R. C., C. Hedberg, and K. White. 1991. A multistate outbreak of *Salmonellajavian* infections associated with raw tomatoes. Presented at the CDC Epidemic Intelligence Service, 40th Annual Conference, Atlanta, Ga.

Zepeda-Lopez, H., M. Ortega-Rodriquez, E. I. Quinonez-Ramirez, and C. Vazguez-Salinas. 1995. Isolation of *Escherichia coli* O157:H7 from vegetables. Presented at the American Society for Microbiology Annual Meeting, Washington, D.C.

Zhuang, R. Y., L. R. Beuchat, and F. J. Angulo. 1995. Fate of Salmonella montevideo in raw tomatoes as affected by temperature and treatment with chlorine. Appl. Environ. Microbiol. 61:2127–2131.

What is claimed is:

1. A biosensor/bioreporter device for detecting a bacterial target cell population comprising:
   (a) a genetically engineered bacterial bioluminescent bioreporter cell population responsive to an inducer;
   (b) at least one bacteriophage capable of specifically infecting said bacterial target cell but not the bioreporter cell, said bacteriophage being genetically modified to cause the target cell to express said inducer upon infection of the target cell; and
   (c) at least one container suitable for housing the bioreporter cell population, target cell population and bacteriophage, said container being operably connected to a light measuring device selected from the group consisting of an integrated circuit, a photomultiplier tube, a photodiode, a microchannel plate, and a charge-coupled device, said light-measuring device being adapted to detect a bioluminescent signal generated in said container upon interaction of the bioreporter cell population and the inducer, wherein detecting the bioluminescent signal is correlated with detecting the presence of the target cell.

2. The biosensor/bioreporter device of claim 1 wherein the genetically engineered bioluminescent bioreporter cell population contains a luxR-$lux_{pro}$/lux I/luxCDABE gene construct.

3. The biosensor/bioreporter device of claim 1 wherein the genetically modified bacteriophage contains a luxI gene.

4. The biosensor/bioreporter device of claim 1 wherein the infected target cell expresses a luxI gene product that induces the bioreporter cells to produce light.

5. The device of claim 1 wherein the genetically modified bacteriophage comprises a plurality of genetically modified bacteriophage, each specifically infecting a different target bacterium.

6. The device of claim 1 wherein the target bacterium is selected from the group consisting of Salmonella, Vibrio, Pseudomonas, Escherichia, Bacillus, Clostridium, Yersinia, Shigella, Legionella, Burkholderia, Staphylococcus, Streptococcus, Proteus, Enterobacter, Mycobacterium, Campylobacter, and Listeria.

7. The device of claim 1 wherein the genetically engineered bioreporter cells are *E. coli*.

8. A system comprising the device of claim 1, an automatic sampling device and an analysis component for data processing.

9. The device of claim 1 wherein the genetically engineered bioreporter cells are selected from the group consisting of Escherichia, Pseudomonas, Vibrio, Staphylococcus, Alcaligenes, Acinetobacter, Synechococcus, *Aeromonas hydrophila* and Ralstonia.

10. The device of claim 9 wherein the bioreporter cell population is held in an encapsulation matrix.

11. The device of claim 10 wherein the encapsulation matrix is alginate, carrageenan, acrylic vinyl acetate copolymer, latex, polyvinyl chloride polymer, sol-gel, agar, agarose, micromachined nanoporous membranes, polydimethylsiloxane (PDMS), polyacrylamide, polyurethane/polycarbomyl sulfonate, or polyvinyl alcohol.

12. The device of claim 1 wherein the light measuring device is an integrated circuit.

13. The device of claim 12 wherein the integrated circuit comprises a photodetector and low-noise electronics.

14. The device of claim 1 or 12 wherein the container and the light measuring device are housed in a single unit.

15. A method of detecting a selected target bacterium, comprising:
   providing a genetically engineered bacterial bioluminescent bioreporter cell population responsive to an inducer;
   providing a modified bacteriophage capable of specifically infecting said target bacterium but not the biorporter cells, said bacteriophage being genetically modified to cause the target bacterium to express said inducer upon infection of the target bacterium, and
   contacting a sample suspected of containing said target bacterium with said bacteriophage together with a population of said bioreporter bacterial cells,
   wherein a detectable bioluminescent signal is induced in said cell population subsequent to infection of the target bacterium with the bacteriophage, said detectable bioluminescent signal being correlated the presence of the target bacterium.

16. The method of claim 15 wherein said genetically modified bioreporter cells are modified to contain a luxR-$lux_{pro}$/luxI/luxCDABE gene construct and said modified bacteriophage is a luxI-genetically modified bacteriophage.

17. The method of claim 15 wherein the selected target bacterium is selected from The group consisting of *Escherichia coli, Listeria monocytogenes*, Salmonella spp., Campylobacter spp., *B. anthracis, B. thuringiensis* and *B. subtilis*.

18. The method of claim 15 wherein the bioreporter bacterial cells are selected from the group consisting of Escherichia, Pseudomonas, Vibrio, Staphylococcus, Alcaligenes, Acinetobacter, Synechococcus, *Aeromonas hydrophila* and Ralstonia.

19. The method of claim 15 wherein the bioreporter bacterial cells are *Pseudomonas fluorescens*.

20. A method of determining the amount of a selected bacterium in a sample comprising:
   contacting a sample suspected of containing a selected bacterium with:
   (a) a bacterium-specific bacteriophage genetically modified to cause the bacterium to express an inducer upon infection of the bacterium; and
   (b) a population of bacterial bioreporter cells responsive to the inducer;
   wherein the amount of the selected bacterium is determined by measuring the time required for production of a selected intensity of bioluminescent signal by the bioreporter cell population in the presence and in the absence of the selected bacterium; and relating the amount of said selected bacterium to the difference in time required for production of the selected intensity of bioluminescent signal by the bioreporter cell population in the presence and in the absence of the bacterium.

21. A kit for detection of selected bacteria, comprising in suitable container form:
   (a) a genetically engineered bacteriophage that harbors a luxI gene and specifically infects a selected bacterium;
   (b) a bioreporter cell population genetically engineered to include a luxR-$lux_{pro}$/luxI/luxCDABE gene construct, said bioreporter being incapable of infection by said bacteriophage; and
   (c) instructions for use.

22. A kit for detection of a target bacterial cell comprising in suitable package form:
   (a) a genetically engineered bacteriophage that harbors a luxI gene and specifically infects a selected bacterium;

(b) a bioreporter cell population genetically engineered to include a luxR-lux$_{pro}$/luxI/luxCDABE gene construct, said bioreporter being incapable of infection by said bacteriophage; and (c) a device for measurement of generated light, said device comprising at least one container suitable for housing the bioreporter cell population, target cell population and bacteriophage, said container being operably connected to an integrated circuit adapted for detecting a luminescent signal produced when a bacteriophage-infected target cell induces a bioluminescent protein in the bioreporter cell population; and (d) instructions for use.

23. A composition comprising:

a bacterial bioreporter cell population genetically modified to contain a luxR-lux$_{pro}$/luxI/luxCDABE gene construct; and a luxI-modified bacteriophage selective for an identified bacterium but not said bacterial bioreporter cell population.

24. The composition of claim 23 wherein the bacterial cell population is *E. coli*.

25. The composition of claim 23 wherein the bacteriophage is M13.

26. The composition of claim 23 wherein the luxI modified bacteriophage comprises a plurality of bacteriophage, each specific for a different bacterial cell host.

27. A biosensor/bioreporter device for detecting a bacterial target cell population comprising:

(a) a bacterial bioluminescent bioreporter cell population responsive to an acyl-homoserine lactone inducer, said bioreporter containing a luxR-lux$_{pro}$/luxI/luxCDABE gene construct;

(b) at least one bacteriophage capable of specifically infecting the bacterial target cell but not the bioreporter cell, said bacteriophage being genetically modified to cause the target cell to express said acyl-homoserine lactone inducer upon infection of the target cell; and (c) at least one container suitable for housing the bioreporter cell population, target cell population and bacteriophage, said container being operably connected to an integrated circuit adapted to detect a bioluminescent signal generated in said container upon interaction of the bioreporter cell population and the inducer, wherein detecting the bioluminescent signal is correlated with detecting the presence of the target cell.

* * * * *